United States Patent [19]
Holtzman

[11] Patent Number: 5,942,420
[45] Date of Patent: Aug. 24, 1999

[54] MOLECULES OF THE FOLLISTATIN-RELATED PROTEIN FAMILY AND USES THEREFOR

[75] Inventor: Douglas A. Holtzman, Cambridge, Mass.

[73] Assignee: Millennium BioTherapeutics, Inc., Cambridge, Mass.

[21] Appl. No.: 08/972,008

[22] Filed: Nov. 17, 1997

[51] Int. Cl.$^6$ .......................... C12P 21/06; C07H 21/02; C07H 21/04; C12N 15/00

[52] U.S. Cl. ................ 435/69.1; 435/252.3; 435/254.11; 435/325; 435/320.1; 536/23.1; 536/23.5; 935/22

[58] Field of Search .............................. 435/69.1, 320.1, 435/252.3, 254.11, 325; 536/23.1, 23.5; 935/22

[56] References Cited

FOREIGN PATENT DOCUMENTS

WO89/01945  3/1989  WIPO.

OTHER PUBLICATIONS

Amthor, H. et al. "The Expression and Regulation of Follistatin and a Follistatin–like Gene during Aviation Somite Compartmentalization and Myogenesis" *Developmental Biology* 178:343–362 (1996).

Besecke, L.M. et al. "Pituitary Follistatin Regulates Activin–Mediated Production of Follicle–Stimulating Hormone during the Rat Estrous Cycle" *Endocrinology* 138(7):2841–2848 (1997).

DePaolo, L.V. et al. "Follistatin and Activin: A Potential Intrinsic Regulatory System within Diverse Tissues" *Proceedings of the Society for Experimental Biological and Medicine* 198:500–512 (1991).

DePaolo, L.V. "Inhibins, Activins, and Follistatins: The Saga Continues" *Proceedings of the Society for Experimental Biological and Medicine* 214:328–339 (1997).

Eib, D.W. et al. "A Novel Transmembrane Protein with Epidermal Growth Factor and Follistatin Domains Expressed in the Hypothalamo–Hypophysial Axis of *Xenopus laevis*" *Journal of Neurochemistry* 67:1047–1055 (1996).

Esch, F.S. et al. "Structural Characterization of Follistatin: A Novel Follicle–Stimulating Hormone Release–Inhibiting Polypeptide for the Gonad" *Molecular Endocrinology* 1(11):849–855.

Hashimoto, O. et al. "A Novel Role of Follistatin, an Activin–binding Protein, in the Inhibition of Activin Action in Rat Pituitary Cells" *The Journal of Biological Chemistry* 272(21):13835–13842 (1997).

Hohenester, E. et al. "Crystal Structure of a Pair of Follistatin–like and EF–Hand Calcium–Binding Domains in BM–40" *Embo* 16(13):3778–3786 (1977).

Lane, T. et al. "The Biology of SPARC, a Protein that Modulates Cell–Matrix Interactions" *The FASEB Journal* 8:163–173(1994).

Link, B.A. et al. "Opposing Effects of Activin A and Follistatin on Developing Skeletal Muscle Cells" *Experimental Cell Research* 233:350–362 (1997).

Michel, U. et al. "Follistatins: More than Follicle–Stimulating Hormone Suppressing Proteins" *Molecular and Cellular Biology* 91:1–11 (1993).

Patel, K. et al. "Cloning and Early Dorsal Axial Expression of Flik, a Chick Follistatin–Related Gene: Evidence for Involvement in Dorsalization/Neural Induction" *Developmental Biology* 178:327–342 (1996).

Petralia, F. "Inhibin, Activin and Follistatin in the Human Placenta—a New Family of Regulatory Proteins" *Placenta* 18:3–8 (1997).

Patthy, L. et al. "Functions of Agrin and Agrin–related Proteins" *TINS* 16(2):76–81 (1993).

Sakamoto, Y. et al. "Determination of Free Follistatin Levels in Sera of Normal Subjects and Patients with Various Diseases" *European Journal of Endocrinology* 135:345–351 (1996).

Shibanuma, M. et al. "Cloning from a Mouse Osteoblastic Cell Line of a Set of Transforming–growth–factor–$\beta$1–regulated Genes, One of which Seems to Encode a Follistatin–related Polypeptide" *European Journal of Biochemistry* 217:13–19 (1993).

Shimonaka, M. et al. "Follistatin Binds to both Activin and Inhibin through the Common Beta–Subunit" *Endocrinology* 128(6):3313–3315 (1991).

Zwijsen, A. et al. "Characterization of a Rat $C_6$ Glioma–secreted Follistatin–related Protein (FRP): Cloning and Sequence of the Human Homologue" *European Journal of Biochemistry* 225:937–946 (1994).

*Primary Examiner*—Robert A. Wax
*Assistant Examiner*—Einar Stole
*Attorney, Agent, or Firm*—Jean M. Silveri; Lahive & Cockfield, LLP; Amy E. Mandragouras

[57] ABSTRACT

Novel FMCP polypeptides, proteins, and nucleic acid molecules are disclosed. In addition to isolated, full-length FMCP proteins, the invention further provides isolated FMCP fusion proteins, antigenic peptides and anti-FMCP antibodies. The invention also provides FMCP nucleic acid molecules, recombinant expression vectors containing a nucleic acid molecule of the invention, host cells into which the expression vectors have been introduced and non-human transgenic animals in which a FMCP gene has been introduced or disrupted. Diagnostic, screening and therapeutic methods utilizing compositions of the invention are also provided.

64 Claims, 6 Drawing Sheets

Fig. 1A

```
                                                    M   R   P   G   A   P   G   P   L   W
  10  CGCTGCCGTCTCTGCGTTCGCC ATG CGT CCC GGG GCG CCA GGG CCA CTC TGG
  69

P   L   P   W   G   A   L   A   W   A   V   G
  30  CCT CTG CCC TGG GGG GCC CTG GCT TGG GCC GTG GGG
 129

F   V   S   M   G   S   G
  50  TTC GTG AGC TCG ATG GGC TCG GGG

P   A   P   G   V   C   W   L   Q   Q   Q   G   E   A   T   C   S   L
 189  CCC GCG CCC GGT GGT GTT TGC TGG CTC CAG CAG CAG GGC GAG GCC ACC TGC AGC CTG

Q   T   D   V   T   R   A   E   C   C   A   S   G   N   I   D   T   A
  70  CTC CAG ACT GAT GTC ACC CGG GCC GAG TGC TGT GCC TCC GGC AAC ATT GAC ACC GCC
 249

N   L   T   H   P   G   N   K   I   N   L   L   G   F   L   G   L   V
  90  AAC CTC ACC CAC CCG GGG AAC AAG ATC AAC CTC CTC GGC TTC TTG GGC CTT GTC
 309

P   C   K   D   S   C   D   G   V   E   C   G   P   G   K   A   C
 110  CCC TGC AAA GAT TCG TGC GAC GGC GTG GAG TGC GGC CCG GGC AAG GCG TGC
 369
```

```
R    M    L    G    R    P    R    C    E    C    A    P    D    C    S    G    L    P    A
130
CGC  ATG  CTG  GGG  GGC  CGC  CCG  CGC  TGC  GAG  TGC  GCG  CCC  GAC  TGC  TCG  GGG  CTC  CCG  GCG
429

R    L    Q    V    C    G    S    D    P    R    G    C    T    Y    R    D    E    C    E    L    A
150
CTG  CAG  GTC  TGC  GGC  TCA  GAC  CCG  CGC  GGC  TGC  ACC  TAC  CGC  GAC  GAG  TGC  GAG  CTG  GCC

R    C    R    G    H    P    D    L    S    V    M    Y    R    G    R    C    R    K    S
170
GCG  CGC  TGC  CGC  GGC  CAC  CCG  GAC  CTG  AGC  GTC  ATG  TAC  CGG  GGC  CGC  TGC  AAG  TCC
549

C    E    H    V    V    C    P    R    P    Q    S    C    V    D    Q    T    G    S    A
190
TGT  GAG  CAC  GTG  GTG  TGT  CGA  CCG  CGG  CCA  CAG  TCG  TGC  GTC  GAC  CAG  ACG  GGC  AGC  GCC
609

H    C    V    V    C    R    A    A    P    C    P    V    P    S    S    P    G    Q    E    L
210
CAC  TGC  GTG  GTG  TGT  CGA  GCG  GCG  CCC  TGC  CCT  GTG  CCC  TCC  AGC  CCC  GGC  CAG  GAG  CTT
669

G    N    N    V    T    Y    I    S    C    H    M    R    Q    A    T    C    F
230
GGC  AAC  AAC  GTC  ACC  TAC  ATC  TCC  TGC  CAC  ATG  CGC  CAG  GCC  ACC  TGC  TTC
729
```

Fig. 1B

```
 L   G   R   S   I   G   V   R   H   A   G   S   C   A   G   T   P   E   E   P
250
CTG GGC CGC TCC ATC GGC GTG CGC CAC GCG GGC AGC TGC GCA GGC ACC CCT GAG GAG CCG
789

P   G   G   E   S   A   E   E   E   N   F   V   *
264
CCA GGT GGT GAG TCT GCA GAA GAG GAA GAG AAC TTC GTG TGA
831

GCCTGCAGGACAGGCCTGGGCCCTGGTGCCCGAGGCCCCCCATCATCCCCTGTTATTTATTGCCACAGCAGAGTCTAATT
910

TATATGCCACGGACACTCCTTAGAGCCCGGATTCGGACCACTTGGGGGATCCCAGAACCTCCCTGACGATATCCTGGAAG
989

GACTGAGGAAGGGAGGCCTGGGGCCGGCTGGTGGGATAGACCTGCGTTCCGGACACTGAGCGCCTGATTTAGGG
1068

CCCTTCTCTAGGATGCCCCAGCCCCTACCCTAAGACCTATTGCCGGGAGGATTCCACACTTCCTCTCCTTTGGGATA
1147

AACCTATTAATTATTGCTACTATCAAGAGGGCTGGGCATTCTCTGCTGGTAATTCCTGAAGAGGCATGACTGCTTTTCT
1226

CAGCCCCAAGCCTCTAGTCTGGGTGTGTACGAGGGTCTAGCCTGGGTGTGTACGGAGGTCTAGCCTGGGTGAGTACG
1305

GAGGGTCTAGCCTGGGTGAGTACGGAGGGTCTAGCCTGGGTGAGTACGGAGAGTCTAGCCTGGGTGTGTATGGAGGATC
1384
```

Fig. 1C

```
TAGCCTGGGTGAGTATGGAGGGTCTAGCCTGGGTGTGTATGGAGGGTCTAGCCTG
1463
GGTGAGTATGGAGGGTCTAGCCTGGGTGTGTATGGAGGGTCTAGCCTGGGTGTGT
1542
ACGGAGGGTCTAGTCTGAGTGCGTGTGGGGACCTCAGAACACTGTGACCTTCATGAAG
1621
GCCAAGAAGGCTGCCACCATTCCCTGCCAGCCCAAGAACTCCAGCTTCCCCACTGCCTCTGTGTGCCCCTTTGCGTCCT
1700
GTGAAGGCCATTGAGAAATGCCCAGTGTGCCCCCTGGGAAAGGGCACGGCCTGTGCTCCTGACACGGGCTGTGCTTGGC
1779
CACAGAACCACCCCAGCGTCTCCCCTGCTGTGTCCACGTCAGTTCATGAGGCAAVGTCGCGTGGTCTCAGACGTGGAGC
1858
AGCCAGCGGCAGCTCAGAGACCAGGGCACTGTGTCCGGGAGCCAAGTCCACTCTGGGGAGCTCTGGCGGGACCACGG
1937
GCCACTGCTCACCCACTGGCCCCGAGGGGTGTAGACGCCAAGACTCACGCATGTGTGACATCCAGAGTCCTGGAGCC
2016
GGGTGTCCCAGTGGCACCACTAGGTGCCTGCTGCCTCCACAGTGGGGTTCACACCCAGGGCTCCTTGGTCCCCCACAAC
2095
```

Fig. 1D

CTGCCCCGGGCCAGGCCTGCAGACCCAGACTCCAGCCCTGCCTCACCCACCAATGCAGCCGGGGCTGGGCGACACCA
2174

GCCAGGTGCTGGTCTTGGGCCAGTTCTCCCACGACGGGCTCACCCCCTCCATCTGCGTTGATGCTCAGAATCGCCTA
2253

CCTGTGCCTGCGTGTAAACCACAGCCTCAGACCTCAGCTATGGGAGAGGACAACACGGAGGATATCCAGCTTCCCCGGTC
2332

TGGGGTGAGGAGTGTGGGAGCTTGGGCATCCCTCCCTCCAGCCCTCCTCCAGCCCCCCAGGCAGTGCCTTACCTGTGGTGCC
2411

CAGAAAAGTGCCCCTAGGTTGGTGGGTCTACAGGAGCCCAGCCAGGCAGCCCCACCCCTGGGGCCCTGCCTCACC
2490

AAGGAAATAAAGACTCAAAGAAGCCAAAAAAAAAAAAAAAAGGGGCCGC
2542

Fig. 1E

FMCP comparison with Human Follistatin

Gap Weight: 3.000  Average Match: 0.540
Length Weight: 0.100  Average Mismatch -0.396

Quality: 190.2  Length: 347
Ratio: 0.723  Gaps: 6
Percent Similarity: 61.417  Percent Identity: 43.307 follistatinl x t91pro

```
H-Fol    1 MVRARHQP......GGLCLLLLLLCQFMEDRSAQAGNCWLRQAKNGRCQV 44
           | .: ..|        |:|.: : ::: : .:..|.:|  |||.|:.::  | :
FMCP     1 MRPGAPGPLWPLPWGALAWAVGFVSSMGSGNPAPGGVCWLQQGQEATCSL 50

H-Fol   45 LYKTELSKEECCSTGRLSTSWTE..EDVNDNTLFKWMIFNGGAPNCIPCK 92
           :..|::.:.|||..|.:.|.|.:  ...|..|: ::    |.:|:|||
FMCP    51 VLQTDVTRAECCASGNIDTAWSNLTHPGNKINLLGFL....GLVHCLPCK 96

H-Fol   93 ETCENVDCGPGKKCRMNKKNKPRCVCAPDCSNITWKGPVCGLDGKTYRNE 142
           :.|:.|:|||||| |||    .:||| ||||||.:. : .||| || |||:|
FMCP    97 DSCDGVECGPGKACRM.LGGRPRCECAPDCSGLPARLQVCGSDGATYRDE 145

H-Fol  143 CALLKARCKEQPELEVQYQGRCKKTCRDVFCPGSSTCVVDQTNNAYCVTC 192
           |.|   |||:::|:|.|  |.|||:|.|  .|.|| . .|||||||..|.||.|
FMCP   146 CELRAARCRGHPDLSVMYRGRCRKSCEHVVCPRPQSCVVDQTGSAHCVVC 195

H-Fol  193 NRI.CPEPASSEQYLCGNDGVTYSSACHLRKATCLLGRSIGLAYEGKCIK 241
           .   || |.|.:| ||||:.||| |.||:|.|||:|||||||: ..|.|
FMCP   196 RAAPCPVPSSPGQELCGNNNVTYISSCHMRQATCFLGRSIGVRHAGSC.. 243

H-Fol  242 AKSCEDIQCTGGKKCLWDFKVGRGRCSLCDELCPDSKSDEPVCASDNATY 291
           |  ..|: ...::: . :|
FMCP   244 AGTPEEPPGGESAEEEENFV............................. 263
```

Fig. 2

SEQUENCE LISTING

```
(1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 2525 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 23..814

(xi) SEQUENCE DESCRIPTION: SEQ ID NO:1:
```

-continued

| | |
|---|---|
| CGCTGCCGTC TCTGCGTTCG CC ATG CGT CCC GGG GCG CCA GGG CCA CTC TGG<br>                                            Met Arg Pro Gly Ala Pro Gly Pro Leu Trp<br>                                              1               5                     10 | 52 |
| CCT CTG CCC TGG GGG GCC CTG GCT TGG GCC GTG GGC TTC GTG AGC TCC<br>Pro Leu Pro Trp Gly Ala Leu Ala Trp Ala Val Gly Phe Val Ser Ser<br>               15                       20                     25 | 100 |
| ATG GGC TCG GGG AAC CCC GCG CCC GGT GGT GTT TGC TGG CTC CAG CAG<br>Met Gly Ser Gly Asn Pro Ala Pro Gly Gly Val Cys Trp Leu Gln Gln<br>            30                      35                       40 | 148 |
| GGC CAG GAG GCC ACC TGC AGC CTG GTG CTC CAG ACT GAT GTC ACC CGG<br>Gly Gln Glu Ala Thr Cys Ser Leu Val Leu Gln Thr Asp Val Thr Arg<br>         45                      50                    55 | 196 |
| GCC GAG TGC TGT GCC TCC GGC AAC ATT GAC ACC GCC TGG TCC AAC CTC<br>Ala Glu Cys Cys Ala Ser Gly Asn Ile Asp Thr Ala Trp Ser Asn Leu<br> 60                     65                       70 | 244 |
| ACC CAC CCG GGG AAC AAG ATC AAC CTC CTC GGC TTC TTG GGC CTT GTC<br>Thr His Pro Gly Asn Lys Ile Asn Leu Leu Gly Phe Leu Gly Leu Val<br>75                    80                    85                  90 | 292 |
| CAC TGC CTT CCC TGC AAA GAT TCG TGC GAC GGC GTG GAG TGC GGC CCG<br>His Cys Leu Pro Cys Lys Asp Ser Cys Asp Gly Val Glu Cys Gly Pro<br>              95                    100                  105 | 340 |
| GGC AAG GCG TGC CGC ATG CTG GGG GGC CGC CCG CGC TGC GAG TGC GCG<br>Gly Lys Ala Cys Arg Met Leu Gly Gly Arg Pro Arg Cys Glu Cys Ala<br>             110                   115                 120 | 388 |
| CCC GAC TGC TCG GGG CTC CCG GCG CGG CTG CAG GTC TGC GGC TCA GAC<br>Pro Asp Cys Ser Gly Leu Pro Ala Arg Leu Gln Val Cys Gly Ser Asp<br>         125                   130                 135 | 436 |
| GGC GCC ACC TAC CGC GAC GAG TGC GAG CTG CGC GCC GCG CGC TGC CGC<br>Gly Ala Thr Tyr Arg Asp Glu Cys Glu Leu Arg Ala Ala Arg Cys Arg<br>        140                  145                 150 | 484 |
| GGC CAC CCG GAC CTG AGC GTC ATG TAC CGG GGC CGC TGC CGC AAG TCC<br>Gly His Pro Asp Leu Ser Val Met Tyr Arg Gly Arg Cys Arg Lys Ser<br>155                 160                 165                 170 | 532 |
| TGT GAG CAC GTG GTG TGC CCG CGG CCA CAG TCG TGC GTC GTG GAC CAG<br>Cys Glu His Val Val Cys Pro Arg Pro Gln Ser Cys Val Val Asp Gln<br>             175                   180                 185 | 580 |
| ACG GGC AGC GCC CAC TGC GTG GTG TGT CGA GCG GCG CCC TGC CCT GTG<br>Thr Gly Ser Ala His Cys Val Val Cys Arg Ala Ala Pro Cys Pro Val<br>        190                  195                 200 | 628 |
| CCC TCC AGC CCC GGC CAG GAG CTT TGC GGC AAC AAC AAC GTC ACC TAC<br>Pro Ser Ser Pro Gly Gln Glu Leu Cys Gly Asn Asn Asn Val Thr Tyr<br>         205                   210                 215 | 676 |
| ATC TCC TCG TGC CAC ATG CGC CAG GCC ACC TGC TTC CTG GGC CGC TCC<br>Ile Ser Ser Cys His Met Arg Gln Ala Thr Cys Phe Leu Gly Arg Ser<br>        220                  225                 230 | 724 |
| ATC GGC GTG CGC CAC GCG GGC AGC TGC GCA GGC ACC CCT GAG GAG CCG<br>Ile Gly Val Arg His Ala Gly Ser Cys Ala Gly Thr Pro Glu Glu Pro<br>235                 240                 245                 250 | 772 |
| CCA GGT GGT GAG TCT GCA GAA GAG GAA GAG AAC TTC GTG TGAGCCTGCA<br>Pro Gly Gly Glu Ser Ala Glu Glu Glu Glu Asn Phe Val<br>             255                   260 | 821 |
| GGACAGGCCT GGGCCTGGTG CCCGAGGCCC CCCATCATCC CCTGTTATTT ATTGCCACAG | 881 |
| CAGAGTCTAA TTTATATGCC ACGGACACTC CTTAGAGCCC GGATTCGGAC CACTTGGGGA | 941 |
| TCCCAGAACC TCCCTGACGA TATCCTGGAA GGACTGAGGA AGGGAGGCCT GGGGCCGGC | 1001 |
| TGGTGGGTGG GATAGACCTG CGTTCCGGAC ACTGAGCGCC TGATTTAGGG CCCTTCTCTA | 1061 |
| GGATGCCCCA GCCCCTACCC TAAGACCTAT TGCCGGGGAG GATTCCACAC TTCCTCTCCT | 1121 |
| TTGGGGATAA ACCTATTAAT TATTGCTACT ATCAAGAGGG CTGGGCATTC TCTGCTGGTA | 1181 |

```
ATTCCTGAAG AGGCATGACT GCTTTTCTCA GCCCCAAGCC TCTAGTCTGG GTGTGTACGG    1241

AGGGTCTAGC CTGGGTGTGT ACGGAGGGTC TAGCCTGGGT GAGTACGGAG GGTCTAGCCT    1301

GGGTGAGTAC GGAGGGTCTA GCCTGGGTGA GTACGGAGAG TCTAGCCTGG GTGTGTATGG    1361

AGGATCTAGC CTGGGTGAGT ATGGAGGGTC TAGCCTGGGT GAGTATGGAG GGTCTAGCCT    1421

GGGTGTGTAT GGAGGGTCTA GCCTGGGTGA GTATGGAGGG TCTAGCCTGG GTGTGTATGG    1481

AGGGTCTAGC CTGGGTGAGT ATGGAGGGTC TAGCCTGGGT GTGTACGGAG GGTCTAGTCT    1541

GAGTGCGTGT GGGGACCTCA GAACACTGTG ACCTTAGCCC AGCAAGCCAG GCCCTTCATG    1601

AAGGCCAAGA AGGCTGCCAC CATTCCCTGC CAGCCCAAGA ACTCCAGCTT CCCCACTGCC    1661

TCTGTGTGCC CCTTTGCGTC CTGTGAAGGC CATTGAGAAA TGCCCAGTGT GCCCCCTGGG    1721

AAAGGGCACG GCCTGTGCTC CTGACACGGG CTGTGCTTGG CCACAGAACC ACCCAGCGTC    1781

TCCCCTGCTG CTGTCCACGT CAGTTCATGA GGCAACGTCG CGTGGTCTCA GACGTGGAGC    1841

AGCCAGCGGC AGCTCAGAGC AGGGCACTGT GTCCGGCGGA GCCAAGTCCA CTCTGGGGGA    1901

GCTCTGGCGG GGACCACGGG CCACTGCTCA CCCACTGGCC CCGAGGGGGG TGTAGACGCC    1961

AAGACTCACG CATGTGTGAC ATCCAGAGTC CTGGAGCCGG GTGTCCCAGT GGCACCACTA    2021

GGTGCCTGCT GCCTCCACAG TGGGGTTCAC ACCCAGGGCT CCTTGGTCCC CCACAACCTG    2081

CCCCGGCCAG GCCTGCAGAC CCAGACTCCA GCCAGACCTG CCTCACCCAC CAATGCAGCC    2141

GGGGCTGGCG ACACCAGCCA GGTGCTGGTC TTGGGCCAGT TCTCCCACGA CGGCTCACCC    2201

TCCCCTCCAT CTGCGTTGAT GCTCAGAATC GCCTACCTGT GCCTGCGTGT AAACCACAGC    2261

CTCAGACCAG CTATGGGGAG AGGACAACAC GGAGGATATC CAGCTTCCCC GGTCTGGGGT    2321

GAGGAGTGTG GGGAGCTTGG GCATCCTCCT CCAGCCTCCT CCAGCCCCCA GGCAGTGCCT    2381

TACCTGTGGT GCCCAGAAAA GTGCCCCTAG GTTGGTGGGT CTACAGGAGC CTCAGCCAGG    2441

CAGCCCACCC CACCCTGGGG CCCTGCCTCA CCAAGGAAAT AAAGACTCAA AGAAGCCAAA    2501

AAAAAAAAAA AAAAGGGCGG CCGC                                           2525
```

(2) INFORMATION FOR SEQ ID NO:2:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Pro Gly Ala Pro Gly Pro Leu Trp Pro Leu Trp Gly Ala
 1               5                  10                  15

Leu Ala Trp Ala Val Gly Phe Val Ser Ser Met Gly Ser Gly Asn Pro
                20                  25                  30

Ala Pro Gly Gly Val Cys Trp Leu Gln Gln Gly Gln Glu Ala Thr Cys
            35                  40                  45

Ser Leu Val Leu Gln Thr Asp Val Thr Arg Ala Glu Cys Cys Ala Ser
        50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110
```

```
Leu Gly Gly Arg Pro Arg Cys Glu Cys Ala Pro Asp Cys Ser Gly Leu
        115                 120                 125
Pro Ala Arg Leu Gln Val Cys Gly Ser Asp Gly Ala Thr Tyr Arg Asp
130                 135                 140
Glu Cys Glu Leu Arg Ala Ala Arg Cys Arg Gly His Pro Asp Leu Ser
145                 150                 155                 160
Val Met Tyr Arg Gly Arg Cys Lys Ser Cys Glu His Val Val Cys
                165                 170                 175
Pro Arg Pro Gln Ser Cys Val Val Asp Gln Thr Gly Ser Ala His Cys
                180                 185                 190
Val Val Cys Arg Ala Ala Pro Cys Pro Val Pro Ser Ser Pro Gly Gln
                195                 200                 205
Glu Leu Cys Gly Asn Asn Asn Val Thr Tyr Ile Ser Ser Cys His Met
        210                 215                 220
Arg Gln Ala Thr Cys Phe Leu Gly Arg Ser Ile Gly Val Arg His Ala
225                 230                 235                 240
Gly Ser Cys Ala Gly Thr Pro Glu Glu Pro Pro Gly Gly Glu Ser Ala
                245                 250                 255
Glu Glu Glu Glu Asn Phe Val
        260
```

(2) INFORMATION FOR SEQ ID NO:3:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGCGTCCCG GGGCGCCAGG GCCACTCTGG CCTCTGCCCT GGGGGGCCCT GGCTTGGGCC      60
GTGGGCTTCG TGAGCTCCAT GGGCTCGGGG AACCCCGCGC CCGGTGGTGT TTGCTGGCTC     120
CAGCAGGGCC AGGAGGCCAC CTGCAGCCTG GTGCTCCAGA CTGATGTCAC CCGGGCCGAG     180
TGCTGTGCCT CCGGCAACAT TGACACCGCC TGGTCCAACC TCACCCACCC GGGGAACAAG     240
ATCAACCTCC TCGGCTTCTT GGGCCTTGTC CACTGCCTTC CCTGCAAAGA TTCGTGCGAC     300
GGCGTGGAGT GCGGCCCGGG CAAGGCGTGC CGCATGCTGG GGGCCGCCC GCGCTGCGAG     360
TGCGCGCCCG ACTGCTCGGG GCTCCCGGCG CGGCTGCAGG TCTGCGGCTC AGACGGCGCC     420
ACCTACCGCG ACGAGTGCGA GCTGCGCGCC GCGCGCTGCC GCGGCCACCC GGACCTGAGC     480
GTCATGTACC GGGGCCGCTG CCGCAAGTCC TGTGAGCACG TGGTGTGCCC GCGGCCACAG     540
TCGTGCGTCG TGGACCAGAC GGGCAGCGCC CACTGCGTGG TGTGTCGAGC GGCGCCCTGC     600
CCTGTGCCCT CCAGCCCCGG CCAGGAGCTT TGCGGCAACA ACAACGTCAC CTACATCTCC     660
TCGTGCCACA TGCGCCAGGC CACCTGCTTC CTGGGCCGCT CCATCGGCGT GCGCCACGCG     720
GGCAGCTGCG CAGGCACCCC TGAGGAGCCG CCAGGTGGTG AGTCTGCAGA A              771
```

(2) INFORMATION FOR SEQ ID NO:4:

(i) SEQUENCE CHARACTERISTICS:
        (A) LENGTH: 71 amino acids
        (B) TYPE: amino acid
        (D) TOPOLOGY: linear (ii) MOLECULE TYPE: peptide (v) FRAGMENT TYPE: internal -continued (xi) SEQUENCE DESCRIPTION: SEQ ID NO:4:

```
Asp Ser Cys Asp Gly Val Glu Cys Gly Pro Gly Lys Ala Cys Arg Met
1               5                   10                  15

Leu Gly Gly Arg Pro Arg Cys Glu Cys Ala Pro Asp Cys Ser Gly Leu
            20                  25                  30

Pro Ala Arg Leu Gln Val Cys Gly Ser Asp Gly Ala Thr Tyr Arg Asp
        35                  40                  45

Glu Cys Glu Leu Arg Ala Ala Arg Cys Arg Gly His Pro Asp Leu Ser
        50                  55                  60

Val Met Tyr Arg Gly Arg Cys
65                  70
```

(2) INFORMATION FOR SEQ ID NO:5:

(i) SEQUENCE CHARACTERISTICS:
        (A) LENGTH: 73 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Cys Glu His Val Val Cys Pro Arg Pro Gln Ser Cys Val Val Asp Gln
1               5                   10                  15

Thr Gly Ser Ala His Cys Val Val Cys Arg Ala Ala Pro Cys Pro Val
            20                  25                  30

Pro Ser Ser Pro Gly Gln Glu Leu Cys Gly Asn Asn Asn Val Thr Tyr
        35                  40                  45

Ile Ser Ser Cys His Met Arg Gln Ala Thr Cys Phe Leu Gly Arg Ser
        50                  55                  60

Ile Gly Val Arg His Ala Gly Ser Cys
65                  70
```

MOLECULES OF THE FOLLISTATIN-RELATED PROTEIN FAMILY AND USES THEREFOR

BACKGROUND OF THE INVENTION

Follistatin is a single-chain glycoprotein of 35 kDa which is composed of four cysteine-rich domains, three of which are homologous and highly conserved. (Lane et al. (1994) *The FASEB Journal* 8:163–173; Esch et al. (1987) *Mol. Endo.* 1:849–855; Sugano et al. (1994) *Frontiers in Endocrinology* Vol. 3: *Inhibin and Inhibin-related Proteins*, Rome: Ares-Serono Symposia, 69–80). Follistatin domains have recently been described in several mosaic proteins, including agrin (Rupp et al. (1991) *Neuron* 6:811–823), osteonectin/SPARC (Lankat-Buttgereit et al. (1988) *FEBS Lett.* 236:352–356), and the brain-specific extracellular matrix glycoprotein, SC1 (Johnston et al. (1990) *Neuron* 2:165–176; see also, Patthy et al. (1993) *Trends Neurosci.* 16:76–81). It has been proposed that modules donated to mosaic proteins retain the function they had in the donor protein. (Eib et al. (1996) *J. Neurochem.* 67(3) 1047–1055).

Follistatin binds the transforming growth factor-β (TGF-β) family members activin-A and inhibin. (Michel et al. (1993) *Molecular and Cellular Endocrinology* 91:1–11). The family of TGF-β proteins includes, among others, activin-A and inhibin. (Eib et al. (1996) *J. Neurochem.* 67:1047–1055). Members of the TGF-β family are multifunctional cytokines with physiological effects on the growth and differentiation of a variety of normal and neoplastic cells (Sporn et al. (1992) *J. Cell. Biol.* 119:1017–1021). It has been proposed that follistatin and other follistatin-related molecules act by regulating the availability of TGF-β-related and/or other growth factors thereby influencing cellular migration, proliferation, and differentiation (Amthor (1996) *Dev. Biol.* 178:343–361).

Follistatin and follistatin-related molecules have been found to modulate a variety of biological processes. For example, follistatin has been identified as a regulator of pituitary follice stimulating hormone (FSH) secretion (Ueno et al. (1990) *Progress in Growth Factor Research* 2:113–124; Besecke et al. (1997) *Endocrinology* 138:2841–2848). Follistatins have also been characterized as growth factors (Vale et al. (1988) *Recent Progress in Hormone Research* 44:1–34; Link et al. (1997) *Experimental Cell Research* 233:350–362), and embryo modulators (Huylebroeck et al. (1994) *Frontiers in Endocrinology*, Vol. 3: *Inhibin and Inhibin-related Proteins*, Rome: Ares-Serono Symposia Publications, 271–288; Petraglia (1996)). Osteonectin, which contains a single follistatin domain, binds the platelet-derived growth factor (PDGF), preventing PDGF receptor activation (Raines et al. (1992) *Proc. Natl. Acad. Sci.* 89:1281–1304). Also, the follistatin domains in agrin have been reported to act in binding and thus creating local concentrations of TGF-β family members in motor neurons and muscle (Patthy et al. (1993)). In addition, follistatin has high affinity for heparin sulfate side chains of membrane proteoglycans. (Nakamura et al. (1991) *J. Biol. Chem.* 266:19432–19437).

SUMMARY OF THE INVENTION

The present invention is based, at least in part, on the discovery of novel molecules with a follistatin-like domain, referred to herein ;s "Follistatin-Module-Containing-Protein" (FMCP) and nucleic acid molecules. Thus, the presence of follistatin-related domains in a protein indicates a role in the binding of molecules structurally related to TGF-β family members (Eib et al. (1996) *J. Neurochem.* 67:1047–1055). TGF-β superfamily members are multifunctional cytokines which modulate a number of functions. Therefore, the FMCP molecules of the present invention are useful as modulating agents in regulating a variety of cellular processes. Accordingly, in one aspect, this invention provides isolated nucleic acid molecules encoding FMCP proteins or biologically active portions thereof, as well as nucleic acid fragments suitable as primers or hybridization probes for the detection of FMCP-encoding nucleic acids. In one embodiment, an isolated nucleic acid molecule of the present invention encodes a FMCP protein which includes a follistatin cysteine-rich domain. In another embodiment, the FMCP nucleic acid molecule is a naturally occurring nucleotide sequence.

In another embodiment, a FMCP nucleic acid molecule is 45% homologous to the nucleotide sequence shown in SEQ ID NO:1, SEQ ID NO:3, or the nucleotide sequence of the DNA insert of the plasmid deposited with ATCC as Accession Number 98546, or a complement thereof In a preferred embodiment, an isolated FMCP nucleic acid molecule encodes the amino acid sequence of human FMCP.

In another embodiment, a FMCP nucleic acid includes a nucleotide sequence encoding a protein having an amino acid sequence sufficiently homologous to a follistatin cysteine-rich domain amino acid sequence of SEQ ID NO:2. In a preferred embodiment, a FMCP nucleic acid molecule has the nucleotide sequence shown SEQ ID NO:1, SEQ ID NO:3, or the nucleotide sequence of the DNA insert of the plasmid deposited with ATCC as Accession Number 98546.

In yet another preferred embodiment, a FMCP nucleic acid molecule includes a nucleotide sequence encoding a protein having an amino acid sequence at least 45% homologous to the amino acid sequence of SEQ ID NO:2.

Another embodiment of the invention features isolated FMCP protein having an amino acid sequence 55% homologous to a follistatin cysteine-rich domain of SEQ ID NO:2 (e.g., about amino acid residues 97–243). Another embodiment of the invention features isolated FMCP protein having an amino acid sequence at least about 65%, prefereably 75%, 85%, or 95% homologous to a follistatin cysteine-rich domain of SEQ ID NO:2 (e.g., about amino acid residues 97–243). Yet another embodiment of the invention features isolated FMCP protein having an amino acid sequence at least about 55% homologous to the amino acid sequence of SEQ ID NO:4 or SEQ ID NO:5. Another embodiment of the invention features isolated FMCP protein having an amino acid sequence at least about 65%, preferably 75%, 85%, or 95% homologous to the amino acid sequence of SEQ ID NO:4 or SEQ ID NO:5.

Yet another embodiment of the invention features isolated FMCP protein which is encoded by a nucleic acid molecule having a nucleotide sequence at least about 55% homologous to a follistatin cysteine-rich domain of SEQ ID NO:2 (e.g., about nucleotides 311 to 751 of SEQ ID NO:1). Another embodiment of the invention features isolated FMCP protein which is encoded by a nucleic acid molecule having a nucleotide sequence at least about 65%, preferably 75%, 85%, or 95% homologous to a follistatin cysteine-rich domain of SEQ ID NO:2 (e.g., nucleotides 311 to 751 of SEQ ID NO:1). This invention further features isolated FMCP protein which is encoded by a nucleic acid molecule having a nucleotide sequence which hybridizes under stringent hybridization conditions to a nucleic acid molecule comprising the nucleotide sequence of SEQ ID NO:1 (e.g., about nucleotides 311 to 751 of SEQ ID NO:1).

In another embodiment, an isolated nucleic acid molecule of the present invention encodes a FMCP protein which includes a signal sequence and is secreted. In another embodiment, an isolated nucleic acid molecule of the present invention encodes a FMCP protein which includes a signal sequence and is retained in an intracellular compartment. In another embodiment, the FMCP nucleic acid molecule encodes a FMCP protein and is a naturally occurring nucleotide sequence.

Another embodiment of the invention features FMCP nucleic acid molecules which specifically detect FMCP nucleic acid molecules relative to nucleic acid molecules encoding other molecules with follistatin-like domains. For example, in one embodiment, a FMCP nucleic acid molecule hybridizes under stringent conditions to a nucleic acid molecule comprising the nucleotide sequence of nucleotides 23 to 811 of SEQ ID NO:1 as shown in SEQ ID NO:3. In another embodiment, the FMCP nucleic acid molecule is at least 500 nucleotides in length and hybridizes under stringent conditions to a nucleic acid molecule comprising the nucleotide sequence shown in SEQ ID NO:1, SEQ ID NO:3, or the nucleotide sequence of the DNA insert of the plasmid deposited with ATCC as Accession Number 98546, or a complement thereof.

In a preferred embodiment, an isolated FMCP nucleic acid molecule comprises nucleotides 311–523 of SEQ ID NO:1 as shown in SEQ ID NO:4 which encodes one follistatin cysteine-rich domain of FMCP, or a complement thereof. In another preferred embodiment, an isolated FMCP nucleic acid molecule comprises nucleotides 533–751 of SEQ ID NO:1 as shown in SEQ ID NO:5 which encodes a second follistatin cysteine-rich domain of FMCP, or complement thereof. In another embodiment, a FMCP nucleic acid molecule further comprises nucleotides 1–523 of SEQ ID NO:1. In another embodiment, a FMCP nucleic acid molecule further comprises nucleotides 1–751. In yet another preferred embodiment, a FMCP nucleic acid molecule further comprises nucleotides 311–2525 of SEQ ID NO:1.

Another embodiment the invention provides an isolated nucleic acid molecule which is antisense to the coding strand of a FMCP nucleic acid.

Another aspect of the invention provides a vector comprising a FMCP nucleic acid molecule. In certain embodiments, the vector is a recombinant expression vector. In another embodiment the invention provides a host cell containing a vector of the invention. The invention also provides a method for producing FMCP protein by culturing in a suitable medium, a host cell of the invention containing a recombinant expression vector such that FMCP protein is produced.

Another aspect of this invention features isolated or recombinant FMCP proteins and polypeptides. In one embodiment, an isolated FMCP protein has a follistatin cysteine-rich domain and is soluble or secreted or retained in an intracellular compartment and lacks a transmembrane or cytoplasmic domain. In another embodiment, an isolated FMCP protein has an amino acid sequence sufficiently homologous to a follistatin cysteine-rich domain amino acid sequence of SEQ ID NO:2. In a preferred embodiment, a FMCP protein has the amino acid sequence of SEQ ID NO:2.

Another embodiment of the invention features isolated FMCP protein having an amino acid sequence at least about 45% homologous to the amino acid sequence of SEQ ID NO:2. Another embodiment of the invention features isolated FMCP protein having an amino acid sequence at least about 55% homologous to the amino acid sequence of SEQ ID NO:2. Another embodiment of the invention features isolated FMCP protein having an amino acid sequence at least about 65% homologous to the amino acid sequence of SEQ ID NO:2. Another embodiment of the invention features isolated FMCP protein having an amino acid sequence at least about 75% homologous to the amino acid sequence of SEQ ID NO:2. Yet another embodiment of the invention features isolated FMCP protein having an amino acid sequence at least about 85% homologous to the amino acid sequence of SEQ ID NO:2. Yet another embodiment of the invention features isolated FMCP protein having an amino acid sequence at least about 95% homologous to the amino acid sequence of SEQ ID NO:2. Yet another embodiment of the invention features isolated FMCP protein which is encoded by a nucleic acid molecule having a nucleotide sequence at least about 45% homologous to a nucleotide sequence of SEQ ID NO:1, SEQ ID NO:3, or the nucleotide sequence of the DNA insert of the plasmid deposited with ATCC as Accession Number 98546 or a complement thereof. This invention further features isolated FMCP protein which is encoded by a nucleic acid molecule having a nucleotide sequence which hybridizes under stringent hybridization conditions to a nucleic acid molecule comprising the nucleotide sequence of SEQ ID NO:1, SEQ ID NO:3, or the nucleotide sequence of the DNA insert of the plasmid deposited with ATCC as Accession Number 98546.

Another embodiment of the invention features isolated FMCP protein having an amino acid sequence 55% homologous to a follistatin cysteine-rich domain of SEQ ID NO:2 (e.g., about amino acid residues 97–243). Another embodiment of the invention features isolated FMCP protein having and amino acid sequence at least about 65%, preferably 75%, 85%, or 95% homologous to a follistatin cysteine-rich domain of SEQ ID NO:2 (e.g., about amino acid residues 97–243). Yet another embodiment of the invention features isolated FMCP protein having an amino acid sequence at least about 55% homologous to the amino acid sequence of SEQ ID NO:4 or SEQ ID NO:5. Another embodiment of the invention features isolated FMCP protein having an amino acid sequence at least about 65%, preferably 75%, 85%, or 95% homologous to the amino acid sequence of SEQ ID NO:4 or SEQ ID NO:5.

Yet another embodiment of the invention features isolated FMCP protein which is encoded by a nucleic acid molecule having a nucleotide sequence at least about 55% homologous to a follistatin cysteine-rich domain of SEQ ID NO:2 (e.g., about nucleotides 311 to 751 of SEQ ID NO:1). Another embodiment of the invention features isolated FMCP protein which is encoded by a nucleic acid molecule having a nucleotide sequence at least about 65%, preferably 75%, 85%, or 95% homologous to a follistatin cysteine-rich domain of SEQ ID NO:2 (e.g., nucleotides 311 to 751 of SEQ ID NO:1). This invention further features isolated FMCP protein which is encoded by a nucleic acid molecule having a nucleotide sequence which hybridizes under stringent hybridization conditions to a nucleic acid molecule comprising the nucleotide sequence of SEQ ID NO:1 (e.g., about nucleotides 311 to 751 of SEQ ID NO:1).

The FMCP proteins of the present invention, or biologically active portions thereof, can be operatively linked to a non-FMCP polypeptide to form FMCP fusion proteins. The invention further features antibodies that specifically bind FMCP proteins, such as monoclonal or polyclonal antibodies. In addition, the FMCP proteins or biologically active portions thereof can be incorporated into pharmaceutical compositions, which optionally include pharmaceutically acceptable carriers.

In another aspect, the present invention provides a method for detecting the presence of FMCP activity or expression in a biological sample by contacting the biological sample with an agent capable of detecting an indicator of FMCP activity such that the presence of FMCP activity is detected in the biological sample.

In another aspect, the invention provides a method for modulating FMCP activity comprising contacting the cell with an agent that modulates FMCP activity such that FMCP activity in the cell is modulated. In one embodiment, the agent inhibits FMCP activity. In another embodiment, the agent stimulates FMCP activity. In one embodiment, the agent is an antibody that specifically binds to FMCP protein. In another embodiment, the agent modulates expression of FMCP by modulating transcription of a FMCP gene or translation of a FMCP mRNA. In yet another embodiment, the agent is a nucleic acid molecule having a nucleotide sequence that is antisense to the coding strand of the FMCP mRNA or the FMCP gene.

In one embodiment, the methods of the present invention are used to treat a subject having a disorder characterized by aberrant FMCP protein or nucleic acid expression or activity by administering an agent which is a FMCP modulator to the subject. In one embodiment, the FMCP modulator is a FMCP protein. In another embodiment the FMCP modulator is a FMCP nucleic acid molecule. In yet another embodiment, the FMCP modulator is a peptide, peptidomimetic, or other small molecule. In a preferred embodiment, the disorder characterized by aberrant FMCP protein or nucleic acid expression is a proliferative or differentiative disorder.

The present invention also provides a diagnostic assay for identifying the presence or absence of a genetic lesion characterized by at least one of (i) aberrant modification or mutation of a gene encoding a FMCP protein; (ii) misregulation of said gene; and (iii) aberrant post-translational modification of a FMCP protein, wherein a wild-type form of said gene encodes an protein with a FMCP activity.

In another aspect the invention provides a method for identifying a compound that binds to or modulates the activity of a FMCP protein, by providing a indicator composition comprising a FMCP protein having FMCP activity, contacting the indicator composition with a test compound, and determining the effect of the test compound on FMCP activity in the indicator composition to identify a compound that modulates the activity of a FMCP protein.

Other features and advantages of the invention will be apparent from the following detailed description and claims.

BRIEF DESCRIPTION OF THE DRAWINGS

FIG. 1 depicts the cDNA sequence and predicted amino acid sequence of human FMCP (also referred to as "TANGO 91"). The nucleotide sequence corresponds to nucleic acids 1 to 2525 of SEQ ID NO:1 which includes the 5' and 3' untranslated regions or SEQ ID NO:3 which corresponds to the open reading frame (nucleotides 23– 811 of SEQ ID NO:1). The amino acid sequence of FMCP corresponds to amino acids 1 to 263 of SEQ ID NO:2.

FIG. 2 depicts an alignment of the amino acid sequences of human FMCP (corresponding to amino acids 97 to 243 of SEQ ID NO:2) and human follistatin cysteine-rich domain (Swiss-Prot™ Accession No. P19883). Alignment of the human FMCP protein with the human follistatin protein using Wisconsin GCG sequence alignment program GAP revealed that FMCP is 43% identical and 61% similar to the human follistatin gene. This alignment included a Gap Weight of 3.0 and a Length Weight of 0.1.

DETAILED DESCRIPTION OF THE INVENTION

The present invention is based on the discovery of novel molecules having at least one follistatin cysteine-rich domain, referred to herein as FMCP (Follistatin Module Containing Protein) and nucleic acid molecules, which comprise a family of molecules having certain conserved structural and functional features. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a FMCP family is identified based on the presence of at least one "follistatin cysteine-rich domain" in the protein or corresponding nucleic acid molecule. As used herein, the term "follistatin cysteine-rich domain" refers to a protein domain having an amino acid sequence of about 30 to 200 amino acid residues in length, of which at least about 3 and up to about 20 amino acids are the amino acid residue cysteine. More preferably, the follistatin cysteine-rich domain is at least about 40 to about 150 amino acid residues in length, of which at least about 4 and up to about to 15 amino acids are the amino acid cysteine. More preferably., the follistatin cysteine-rich domain is at least about 50 to about 130 amino acid residues in length, of which at least about 5 and up to about 13 amino acids are the amino acid cysteine. More preferably, the follistatin cysteine-rich domain is at least about 60 to 110 amino acid residues in length of which at least about 6 and up to about 11 amino acid residues are the amino acid cysteine. More preferably, the follistatin cysteine-rich domain is at least about 70 to 90 amino acid residues in length of which at least about 7 and up to about 9 amino acid residues are the amino acid cysteine. Preferably, the follistatin cysteine-rich domain contains at least 10 cysteine residues.

Preferably, the follistatin cysteine-rich domain of FMCP has cysteine residues which are located in the domain in the same or similar positions as cysteine residues in a follistatin cysteine-rich domain of a related FMCP family member or FMCP homolog. For example, when a FMCP protein of the invention is aligned with a FMCP family member or homolog for purposes of comparison (see e.g., FIG. 2) preferred cysteine-rich domains of the invention are those in which cysteine residues in the amino acid sequence of FMCP are located in the same or similar position as the cysteine residues in the FMCP family member or FMCP homolog. As an illustrative embodiment, FIG. 2 shows cysteine residues located in the same or similar positions of the human follistatin protein and the FMCP protein at the following locations: amino acid number 95 of the human follistatin protein and amino acid number 99 of the FMCP protein; amino acid number 100 of the human follistatin protein and amino acid number 104 of the FMCP protein; and amino acid number 106 of the human follistatin protein and amino acid number 110 of the FMCP protein.

In another embodiment, a FMCP family is identified based on the presence of at least one follastatin cysteine-rich domain in the protein or corresponding nucleic acid molecule in which at least about 10–15% of the amino acid residues of the domain are cysteine residues.

In one embodiment, a FMCP protein includes a cysteine rich domain having at least about 55%, preferably at least about 65%, and more preferably about 75%, 85%, or 95% amino acid sequence homology to a follistatin cysteine-rich domain of SEQ ID NO:2. A preferred follistatin cysteine-rich domain includes amino acid residues 97 to 243 of SEQ ID NO:2. In another embodiment, a follistatin cysteine-rich domain includes amino acid residues 97 to 167 of SEQ ID NO:2 (as shown in SEQ ID NO:4) or amino acid residues 171 to 243 of SEQ ID NO:2 (as shown in SEQ ID NO:5). Preferably, a FMCP protein includes at least two follistatin cysteine-rich domains, more preferably at least three follistatin cysteine-rich domains, and more preferably at least four or five follistatin cysteine-rich domains.

Preferred FMCP molecules of the present invention have an amino acid sequence sufficiently homologous to a follistatin cysteine-rich domain amino acid sequence of SEQ ID NO:2. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 40% homology, preferably 50% homology, more preferably 60%–70% homology are defined herein as sufficiently homologous. In one embodiment, the a FMCP protein contains a follistatin cysteine-rich domain and a FMCP activity.

As used interchangeably herein a "FMCP activity", "biological activity of FMCP" or "functional activity of FMCP", refers to an activity exerted by a FMCP protein, polypeptide or nucleic acid molecule on a FMCP responsive cell as determined in vivo, or in vitro, according to standard techniques. In one embodiment, a FMCP activity is a direct activity, such as an association with or an enzymatic activity on a second protein. In another embodiment, a FMCP activity is an indirect activity, such as a cellular signaling activity mediated by interaction of the FMCP protein with a second protein. In a preferred embodiment, a FMCP activity includes at least one or more of the following activities: (i) complex formation between a FMCP protein and a cytokine; (ii) interaction of a FMCP protein with a protein having substantial homology to the TGF-β family of proteins; (iii) interaction of a FMCP protein with a TGF-β family member protein; and (iv) interaction of a FMCP protein with other proteins. In yet another preferred embodiment, a FMCP activity is at least one or more of the following activities: (i) modulation of TGF-β-related protein activity; (ii) regulation of cellular proliferation; (iii) regulation of cellular differentiation; and (iv) regulation of cell survival.

Accordingly, another embodiment of the invention features isolated FMCP proteins and polypeptides having a FMCP activity. Preferred FMCP proteins have at least one follistatin cysteine-rich domain (and preferably two or more follistatin cysteine-rich domains) and a FMCP activity. In another preferred embodiment, the FMCP protein has at least one follistatin cysteine-rich domain (and preferably two or more follistatin cysteine-rich domains), a FMCP activity and an amino acid sequence sufficiently homologous to an amino acid sequence of SEQ ID NO:2.

Accordingly, in one embodiment, FMCP proteins of the invention contain at least one follistatin cysteine-rich domain (and preferably two or more follistatin cysteine-rich domains) and have an amino acid sequence sufficiently homologous to amino acid sequence of SEQ ID NO:2. In another preferred embodiment, the FMCP protein has at least one follistatin cysteine-rich domain (and preferably two or more follistatin cysteine-rich domains), an amino acid sequence sufficiently homologous to amino acid sequence of SEQ ID NO:2 and a FMCP activity.

Yet another embodiment of the invention features FMCP molecules which contain a signal sequence. As used herein, a "signal sequence" refers to a peptide containing about 20 amino acids which occurs at the extreme N-terminal end of secretory and integral membrane proteins and which contains large numbers of hydrophobic amino acid residues. Such a "signal sequence", also referred to in the art as a "signal peptide", serves to direct a protein containing such a sequence to a lipid bilayer.

In a particularly preferred embodiment, the FMCP protein and nucleic acid molecules of the present invention are human FMCP molecules. A nucleotide sequence of a human FMCP protein is shown in FIG. 1 and in SEQ ID NO:1, SEQ ID NO:3, and the nucleotide sequence of the DNA insert of the plasmid deposited with ATCC as Accession Number 98546. A predicted amino acid sequence of the isolated human FMCP protein is shown in FIG. 1 and in SEQ ID NO:2. In addition, the nucleotide sequence corresponding to the coding region of the human FMCP cDNA (nucleotides 23–811) is represented as SEQ ID NO:3.

The human FMCP cDNA, which is approximately 2525 nucleotides in length including untranslated regions as indicated in SEQ ID NO:1, or which corresponds to the open reading frame as indicated in SEQ ID NO:3, encodes a protein having a molecular weight of approximately 25 kDa (excluding post-translational modifications) and which is approximately 263 amino acid residues in length. The human FMCP protein contains two follistatin cysteine-rich domains. A FMCP follistatin cysteine-rich domain can be found at least, for example, from about amino acids 97–167 of SEQ ID NO:2 (Asp97 to Cys167 of the human FMCP amino acid sequence) and, for example, from about amino acids 171–243 of SEQ ID NO:2 (Cys171 to Cys243 of the human FMCP amino acid sequence). These regions contain amino acid sequences of which at least about 10% of the total amino acid residues are cysteine residues and are located in the same or similar positions as the cysteien residues of the a FMCP homolog, e.g., human follistatin. The human FMCP protein is a secreted protein which lacks a transmembrane domain.

Alignment of the human FMCP protein with the human follistatin protein using Wisconsin GCG sequence alignment program GAP revealed that FMCP is 43% identical and 61% similar to the human follistatin protein. Similarly, when FMCP is aligned with the human follistatin-related gene (hFRP) (Swiss Prot Q12841) using GAP, it shows 24% identity and 48% similarity to hFRP.

Alignment of the follistatin domains of the human FMCP protein (as shown in SEQ ID NO:4 and SEQ ID NO:5) with the follistatin domains of the human follistatin protein using DNASTAR MegAlign alignment program of Lipman-Pearson using a ktuple of 2, a gap penalty of 4, and a gap length penalty of 12, revealed that both follistatin cysteine-rich domains of the FMCP protein are 55% homologous to the human follistatin domains.

A 2.5 kb FMCP mRNA transcript is expressed in human tissues including heart, placenta, lung, liver, skeletal muscle, kidney, pancreas, spleen, prostrate, testis, ovary, small intestine, and colon, with more pronounced expression observed in human placenta, testis, and heart. In addition, a smaller FMCP transcript of approximately 1.4 kb is found in heart, placenta, lung, kidney, and testis.

A GenBank™ search using the human FMCP nucleotide sequence of SEQ ID NO:1, revealed eleven EST sequences, two human, eight mouse, and one rat, which were at least 80% identical to different regions of the nucleotide sequence of SEQ ID NO:1. The EST sequences having greater than 80% identity are listed in Table 1, as well as, the nucleotides of SEQ ID NO:1 to which each EST sequence corresponds. Unless specified otherwise, all EST sequences are annotated.

TABLE 1

| Accession No. | SPECIES | nucleotides of EST | corresponding nucleotides of human FMCP (SEQ ID NO:1 OR SEQ ID NO:3) | % Identity |
|---|---|---|---|---|
| AA020306 | mouse | 97 > 461 | 62-426 | 84 |
| AA015105 | mouse | 76 > 365 | 62-351 | 85 |
| W18317 | mouse | 78 > 343 | 62-327 | 85 |
| W14649 | mouse | 1 > 249 | 165-415 | 86 |
| AA051472 | mouse | 77 > 327 | 62-312 | 84 |
| AA408816 | mouse | 35 > 263 | 489-717 | 91 |
| D31566 (not annotated) | human | 24 > 162 | 598-765 | 96 |
| AA023955 | mouse | 3 < 179 | 577-697 | 84 |
| H32687 | rat | 1 > 176 | 123-298 | 82 |
| AA552990 | human | 1 < 174 | 581-775 | 89 |
| AA020355 | mouse | 23 > 173 | 284-434 | 85 |

Various aspects of the invention are described in farther detail in the following subsections:

I. Isolated Nucleic Acid Molecules

One aspect of the invention pertains to isolated nucleic acid molecules that encode FMCP proteins or biologically active portions thereof, as well as nucleic acid fragments sufficient for use as hybridization probes to identify FMCP-encoding nucleic acids (e.g., FMCP mRNA) and fragments for use as PCR primers for the amplification or mutation of FMCP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FMCP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or the nucleotide sequence of the DNA insert of the plasmid deposited with ATCC as Accession Number 98546, or a complement of any of these nucleotide sequences, can be isolated using standard molecular biology techniques and the sequence information provided herein. Using all or portion of the nucleic acid sequences of SEQ ID NO:1, SEQ ID NO:3, or the nucleotide sequence of the DNA insert of the plasmid deposited with ATCC as Accession Number 98546 as a hybridization probe, FMCP nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FMCP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3, or the nucleotide sequence of the DNA insert of the plasmid deposited with ATCC as Accession Number 98546. The sequence of SEQ ID NO:1, SEQ ID NO:3, or the nucleotide sequence of the DNA insert of the plasmid deposited with ATCC as Accession Number 98546 corresponds to the human FMCP cDNA. These cDNA comprise sequences encoding the human FMCP protein (i.e., "the coding region", from nucleotides 23 to 811 of SEQ ID NO:1), as well as 5' untranslated sequences (nucleotides 1 to 22) and 3' untranslated sequences (nucleotides 812 to 2525 of SEQ ID NO:1).

In another preferred embodiment, an isolated nucleic acid molecule of the invention comprises a nucleic acid molecule which is a complement of the nucleotide sequence shown in SEQ ID NO:1, SEQ ID NO:3, or the nucleotide sequence of the DNA insert of the plasmid deposited with ATCC as Accession Number 98546, or a portion of this nucleotide sequence. A nucleic acid molecule which is complementary to the nucleotide sequence shown in SEQ ID NO:1, SEQ ID NO:3, or the nucleotide sequence of the DNA insert of the plasmid deposited with ATCC as Accession Number 98546 is one which is sufficiently complementary to the nucleotide sequence shown in SEQ ID NO:1, SEQ ID NO:3, or the nucleotide sequence of the DNA insert of the plasmid deposited with ATCC as Accession Number 98546 such that it can hybridize to the nucleotide sequence shown in SEQ ID NO:1, SEQ ID NO:3, or the nucleotide sequence of the DNA insert of the plasmid deposited with ATCC as Accession Number 98546 thereby forming a stable duplex.

In still another preferred embodiment, an isolated nucleic acid molecule of the present invention comprises a nucleotide sequence which is at least about 60–65%, preferably at least about 70–75%, more preferable at least about 80–85%, and even more preferably at least about 90–95% or more homologous to the nucleotide sequence shown in SEQ ID NO:1, SEQ ID NO:3, or the nucleotide sequence of the DNA insert of the plasmid deposited with ATCC as Accession Number 98546, or a portion of this nucleotide sequence.

Moreover, the nucleic acid molecule of the invention can comprise only a portion of the nucleic acid sequence of SEQ ID NO:1, SEQ ID NO:3, or the nucleotide sequence of the DNA insert of the plasmid deposited with ATCC as Accession Number 98546, for example, a fragment which can be used as a probe or primer or a fragment encoding a biologically active portion of FMCP. The nucleotide sequence determined from the cloning of the human FMCP gene allows for the generation of probes and primers designed for use in identifying and/or cloning FMCP homologues in other cell types, e.g. from other tissues, as well as FMCP homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 100, 150, 200, 250, 300, 350 or 400 consecutive nucleotides of SEQ ID NO:1, SEQ ID NO:3, or the nucleotide sequence of the DNA insert of the plasmid deposited with ATCC as Accession Number 98546 sense, of an anti-sense sequence of SEQ ID NO:1, SEQ ID NO:3, or the nucleotide sequence of the DNA insert of the plasmid deposited with ATCC as Accession Number 98546, or of a naturally occurring mutant of SEQ ID NO:1, SEQ ID NO:3, or the nucleotide sequence of the DNA insert of the plasmid deposited with ATCC as Accession Number 98546.

Probes based on the human FMCP nucleotide sequence can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a FMCP protein, such as by measuring a level of a FMCP-encoding nucleic acid in a sample of cells from a subject e.g., detecting FMCP mRNA levels or determining whether a genomic FMCP gene has been mutated or deleted.

A nucleic acid fragment encoding a "biologically active portion of FMCP" can be prepared by isolating a portion of SEQ ID NO:1, SEQ ID NO:3, or the nucleotide sequence of the DNA insert of the plasmid deposited with ATCC as Accession Number 98546 which encodes a polypeptide having a FMCP biological activity (the biological activities of the FMCP proteins have previously been described), expressing the encoded portion of FMCP protein (e.g., by recombinant expression in vitro) and assessing the activity of the encoded portion of FMCP. For example, a nucleic acid fragment encoding a biologically active portion of FMCP includes a follistatin cysteine-rich domain, e.g., amino acid residues 97–243 of SEQ ID NO:2. In another embodiment, a nucleic acid fragment encoding a biologically active portion of FMCP includes a follistatin cysteine-rich domain, e.g., SEQ ID NO:4 or SEQ ID NO:5. In another embodiment, a nucleic acid fragment encoding a biologically active portion of FMCP includes a follistatin cysteine-rich domain includes the DNA encoding such domains, e.g., at least nucleic acids 311–523 of SEQ ID NO:1 which encodes the human FMCP follistatin domain represented by amino acid residues 97–167 of SEQ ID NO:2 (as shown in SEQ ID NO:4) or at least nucleic acids 533–751 of SEQ ID NO:1 which encodes the human FMCP follistatin domain represented by amino acid residues 171–243 of SEQ ID NO:2 (as shown in SEQ ID NO:5).

The invention further encompasses nucleic acid molecules that differ from the nucleotide sequence shown in SEQ ID NO:1, SEQ ID NO:3, or the nucleotide sequence of the DNA insert of the plasmid deposited with ATCC as Accession Number 98546 due to degeneracy of the genetic code and thus encode the same FMCP protein as that encoded by the nucleotide sequence shown in SEQ ID NO:1, SEQ ID NO:3, or the nucleotide sequence of the DNA insert of the plasmid deposited with ATCC as Accession Number 98546. In another embodiment, an isolated nucleic acid molecule of the invention has a nucleotide sequence encoding a protein having an amino acid sequence shown in SEQ ID NO:2.

In addition to the human FMCP nucleotide sequence shown in SEQ ID NO:1, SEQ ID NO:3, or the nucleotide sequence of the DNA insert of the plasmid deposited with ATCC as Accession Number 98546, it will be appreciated by those skilled in the art that DNA sequence polymorphisms that lead to changes in the amino acid sequences of FMCP may exist within a population (e.g., the human population). Such genetic polymorphism in the FMCP gene may exist among individuals within a population due to natural allelic variation. As used herein, the terms "gene" and "recombinant gene" refer to nucleic acid molecules comprising an open reading frame encoding a FMCP protein, preferably a mammalian FMCP protein. Such natural allelic variations can typically result in 1–5% variance in the nucleotide sequence of the FMCP gene. Any and all such nucleotide variations and resulting amino acid polymorphisms in FMCP that are the result of natural allelic variation and that do not alter the functional activity of FMCP are intended to be within the scope of the invention.

Moreover, nucleic acid molecules encoding FMCP proteins from other species, and thus which have a nucleotide sequence which differs from the human sequence of SEQ ID NO:1, SEQ ID NO:3, or the nucleotide sequence of the DNA insert of the plasmid deposited with ATCC as Accession Number 98546 are intended to be within the scope of the invention. Nucleic acid molecules corresponding to natural allelic variants and homologues of the FMCP cDNAs of the invention can be isolated based on their homology to the human FMCP nucleic acids disclosed herein using the human cDNAs, or a portion thereof, as a hybridization probe according to standard hybridization techniques under stringent hybridization conditions. For example, a soluble human FMCP cDNA can be isolated based on its homology to human membrane-bound FMCP. Likewise, a membrane-bound human FMCP cDNA can be isolated based on its homology to soluble human FMCP.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:3, or the nucleotide sequence of the DNA insert of the plasmid deposited with ATCC as Accession Number 98546. In another embodiment, the nucleic acid is at least 30, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the FMCP sequence that may exist in the population, the skilled artisan will further appreciate that changes can be introduced by mutation into the nucleotide sequence of SEQ ID NO:1, SEQ ID NO:3,, thereby leading to changes in the amino acid sequence of the encoded FMCP protein, without altering the functional ability of the FMCP protein. For example, nucleotide substitutions leading to amino acid substitutions at "non-essential" amino acid residues can be made in the sequence of SEQ ID NO:1, SEQ ID NO:3, or the nucleotide sequence of the DNA insert of the plasmid deposited with ATCC as Accession Number 98546. A "non-essential" amino acid residue is a residue that can be altered from the wild-type sequence of FMCP (e.g., the sequence of SEQ ID NO:2) without altering the biological activity, whereas an "essential" amino acid residue is required for biological activity. For example, amino acid residues that are conserved among the FMCP proteins of the present invention, as well as, among the follistatin family of proteins (as indicated by the alignment presented as FIG. 2) are predicted to be particularly unamenable to alteration.

For example, preferred FMCP proteins of the present invention, contain at least one follistatin cysteine-rich domain which are typically conserved regions in FMCP family members and FMCP homologs. As such, these conserved domains are not likely to be amenable to mutation. Other amino acid residues, however, (e.g., those that are not conserved or only semi-conserved among members of the follistatin proteins) may not be essential for activity and thus are likely to be amenable to alteration.

Accordingly, another aspect of the invention pertains to nucleic acid molecules encoding FMCP proteins that contain changes in amino acid residues that are not essential for activity. Such FMCP proteins differ in amino acid sequence from SEQ ID NO:2 yet retain biological activity. In one embodiment, the isolated nucleic acid molecule comprises a nucleotide sequence encoding a protein, wherein the protein comprises an amino acid sequence at least about 45% homologous to the amino acid sequence of SEQ ID NO:2. Preferably, the protein encoded by the nucleic acid molecule is at least about 60% homologous to SEQ ID NO:2, more preferably at least about 70% homologous to SEQ ID NO:2, more preferably at least about 80% homologous to SEQ ID NO:2, even more preferably at least about 90% homologous to SEQ ID NO:2, and most preferably at least about 95% homologous to SEQ ID NO:2.

An isolated nucleic acid molecule encoding a FMCP protein homologous to the protein of SEQ ID NO:2 can be created by introducing one or more nucleotide substitutions, additions or deletions into the nucleotide sequence of SEQ ID NO:1, SEQ ID NO:3, or the nucleotide sequence of the DNA insert of the plasmid deposited with ATCC as Accession Number 98546 such that one or more amino acid substitutions, additions or deletions are introduced into the encoded protein. Mutations can be introduced into SEQ ID NO:1, SEQ ID NO:3, or the nucleotide sequence of the DNA insert of the plasmid deposited with ATCC as Accession Number 98546 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in FMCP is preferably replaced with another amino acid residue from the same side chain family. Alternatively, in another embodiment, mutations can be introduced randomly along all or part of a FMCP coding sequence, such as by saturation mutagenesis, and the resultant mutants can be screened for FMCP biological activity to identify mutants that retain activity. Following mutagenesis of SEQ ID NO:1, SEQ ID NO:3, or the nucleotide sequence of the DNA insert of the plasmid deposited with ATCC as Accession Number 98546, the encoded protein can be expressed recombinantly and the activity of the protein can be determined.

In a preferred embodiment, a mutant FMCP protein can be assayed for (1) the ability to form protein:protein interactions with other follistatin-related proteins, other cell-surface proteins, or biologically active portions thereof, (2) complex formation between a mutant FMCP protein and a FMCP ligand; (3) the ability of a mutant FMCP protein to bind to an intracellular target protein or biologically active portion thereof; (e.g. avidin proteins). In yet another preferred embodiment, a mutant FMCP can be assayed for the ability to perform TGF-β super family member activities, such as, (i) complex formation between a FMCP protein and a cytokine; (ii) interaction of a FMCP protein with a protein having substantial homology to the TGF-β family of proteins; (iii) interaction of a FMCP protein with a TGF-β family member protein; and (iv) interaction of a FMCP protein with other proteins. In yet another preferred embodiment, a FMCP activity is at least one or more of the following activities: (i) modulation of TGF-β-related protein activity; (ii) regulation of cellular proliferation; (iii) regulation of cellular differentiation; and (iv) regulation of cell survival.

In addition to the nucleic acid molecules encoding FMCP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire FMCP coding strand, or to only a portion thereof. In one embodiment, an antisense nucleic acid molecule is antisense to a "coding region" of the coding strand of a nucleotide sequence encoding FMCP. The term "coding region" refers to the region of the nucleotide sequence comprising codons which are translated into amino acid residues (e.g., the coding region of human FMCP corresponds to nucleotides 23–811 of SEQ ID NO:1, as shown in SEQ ID NO:3). In another embodiment, the antisense nucleic acid molecule is antisense to a "noncoding region"

of the coding strand of a nucleotide sequence encoding FMCP. The term "noncoding region" refers to 5' and 3' sequences which flank the coding region that are not translated into amino acids (i.e., also referred to as 5' and 3' untranslated regions).

Given the coding strand sequences encoding FMCP disclosed herein (e.g., SEQ ID NO:1 or SEQ ID NO:3, ), antisense nucleic acids of the invention can be designed according to the rules of Watson and Crick base pairing. The antisense nucleic acid molecule can be complementary to the entire coding region of FMCP mRNA, but more preferably is an oligonucleotide which is antisense to only a portion of the coding or noncoding region of FMCP mRNA. For example, the antisense oligonucleotide can be complementary to the region surrounding the translation start site of FMCP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a FMCP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave FMCP mRNA transcripts to thereby inhibit translation of FMCP mRNA. A ribozyme having specificity for a FMCP-encoding nucleic acid can be designed based upon the nucleotide sequence of a FMCP cDNA disclosed herein (i.e., SEQ ID NO:1, SEQ ID NO:3,). For example, a derivative of a Tetrahymena L-19 IVS RNA can be constructed in which the nucleotide sequence of the active site is complementary to the nucleotide sequence to be cleaved in a FMCP-encoding mRNA. See, e.g., Cech et al. U.S. Pat. No. 4,987,071; and Cech et al. U.S. Pat. No. 5,116,742. Alternatively, FMCP mRNA can be used to select a catalytic RNA having a specific ribonuclease activity from a pool of RNA molecules. See, e.g., Bartel, D. and Szostak, J. W. (1993) *Science* 261:1411–1418.

Alternatively, FMCP gene expression can be inhibited by targeting nucleotide sequences complementary to the regulatory region of the FMCP (e.g., the FMCP promoter and/or enhancers) to form triple helical structures that prevent transcription of the FMCP gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In preferred embodiments, the nucleic acids of FMCP can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *PNAS* 93: 14670–675.

PNAs of FMCP can be used therapeutic and diagnostic applications. For example, PNAs can be used as antisense or antigene agents for sequence-specific modulation of gene expression by, e.g., inducing transcription or translation arrest or inhibiting replication. PNAs of FMCP can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) supra); or as probes or primers for DNA sequence and hybridization (Hyrup B. et al. (1996) supra; Perry-O'Keefe supra).

In another embodiment, PNAs of FMCP can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FMCP can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Research* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxythymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988) or the blood-brain barrier (see, e.g., PCT Publication No. W089/10134, published Apr. 25, 1988). In addition, oligonucleotides can be modified with hybridization-triggered cleavage agents (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated FMCP Proteins and Anti-FMCP Antibodies

One aspect of the invention pertains to isolated FMCP proteins, and biologically active portions thereof, as well as polypeptide fragments suitable for use as immunogens to raise anti-FMCP antibodies. In one embodiment, native FMCP proteins can be isolated from cells or tissue sources by an appropriate purification scheme using standard protein purification techniques. In another embodiment, FMCP proteins are produced by recombinant DNA techniques. Alternative to recombinant expression, a FMCP protein or polypeptide can be synthesized chemically using standard peptide synthesis techniques.

An "isolated" or "purified" protein or biologically active portion thereof is substantially free of cellular material or other contaminating proteins from the cell or tissue source from which the FMCP protein is derived, or substantially free from chemical precursors or other chemicals when chemically synthesized. The language "substantially free of cellular material" includes preparations of FMCP protein in which the protein is separated from cellular components of the cells from which it is isolated or recombinantly produced. In one embodiment, the language "substantially free of cellular material" includes preparations of FMCP protein having less than about 30% (by dry weight) of non-FMCP protein (also referred to herein as a "contaminating protein"), more preferably less than about 20% of non-FMCP protein, still more preferably less than about 10% of non-FMCP protein, and most preferably less than about 5% non-FMCP protein. When the FMCP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of FMCP protein in which the protein is separated from chemical precursors or other chemicals which are involved in the synthesis of the protein. In one embodiment, the language "substantially free of chemical precursors or other chemicals" includes preparations of FMCP protein having less than about 30% (by dry weight) of chemical precursors or non-FMCP chemicals, more preferably less than about 20% chemical precursors or non-FMCP chemicals, still more preferably less than about 10% chemical precursors or non-FMCP chemicals, and most preferably less than about 5% chemical precursors or non-FMCP chemicals.

Biologically active portions of a FMCP protein include peptides comprising amino acid sequences sufficiently homologous to or derived from the amino acid sequence of the FMCP protein, e.g., the amino acid sequence shown in SEQ ID NO:2, which include less amino acids than the full length FMCP proteins, and exhibit at least one activity of a FMCP protein. Typically, biologically active portions comprise a domain or motif with at least one activity of the FMCP protein. A biologically active portion of a FMCP protein can be a polypeptide which is, for example, 10, 25, 50, 100 or more amino acids in length.

In one embodiment, a biologically active portion of a FMCP protein comprises at least one follistatin cysteine-rich domain characteristic of the follistatin family of proteins.

It is to be understood that a preferred biologically active portion of a FMCP protein of the present invention may contain at least one of the above-identified structural domains. A more preferred biologically active portion of a FMCP protein may contain at least two of the above-identified structural domains. An even more preferred biologically active portion of a FMCP protein may contain at least three of the above-identified structural domains. A particularly preferred biologically active portion of a FMCP protein of the present invention may contain at least four of the above-identified structural domains. A more particularly preferred biologically active portion of a FMCP protein may have at least five of the above-identified structural domains. Finally, a most preferred biologically active portion of a FMCP protein may contain at least six of the above-identified structural domains.

Moreover, other biologically active portions, in which other regions of the protein are deleted, can be prepared by recombinant techniques and evaluated for one or more of the functional activities of a native FMCP protein.

In a preferred embodiment, the FMCP protein has an amino acid sequence shown in SEQ ID NO:2. In other embodiments, the FMCP protein is substantially homologous to SEQ ID NO:2 and retains the functional activity of the protein of SEQ ID NO:2 yet differs in amino acid sequence due to natural allelic variation or mutagenesis, as described in detail in subsection II below. Accordingly, in another embodiment, the FMCP protein is a protein which comprises an amino acid sequence at least about 45% homologous to the amino acid sequence of SEQ ID NO:2 and retains the functional activity of the FMCP proteins of SEQ ID NO:2. In another embodiment, the FMCP protein is a protein having an amino acid sequence 55% homologous to a follistatin cysteine-rich domain of SEQ ID NO:2 (e.g., about amino acid residues 97–243, amino acid residues 97–167, or amino acid residues 171–243). Another embodiment of the invention features isolated FMCP protein having and amino acid sequence at least about 65%, prefereably 75%, 85%, or 95% homologous to a follistatin cysteine-rich domain of SEQ ID NO:2 (e.g., about amino acid residues 97–243). Yet another embodiment of the invention features isolated FMCP protein having an amino acid sequence at least about 55% homologous to the amino acid sequence of SEQ ID NO:4 or SEQ ID NO:5. Another embodiment of the invention features isolated FMCP protein having an amino acid sequence at least about 65%, preferably 75%, 85%, or 95% homologous to the amino acid sequence of SEQ ID NO:4 or SEQ ID NO:5. In a preferred embodiment, the FMCP protein retains the functional activity of the FMCP proteins of SEQ ID NO:2.

Yet another embodiment of the invention features isolated FMCP protein which is encoded by a nucleic acid molecule having a nucleotide sequence at least about 55% homologous to a follistatin cysteine-rich domain of SEQ ID NO:2 (e.g., about nucleotides 311 to 751 of SEQ ID NO:1). Another embodiment of the invention features isolated FMCP protein which is encoded by a nucleic acid molecule having a nucleotide sequence at least about 65%, preferably 75%, 85%, or 95% homologous to a follistatin cysteine-rich domain of SEQ ID NO:2 (e.g., nucleotides 311 to 751 of SEQ ID NO:1). This invention further features isolated FMCP protein which is encoded by a nucleic acid molecule having a nucleotide sequence which hybridizes under stringent hybridization conditions to a nucleic acid molecule comprising the nucleotide sequence of SEQ ID NO:1 (e.g., about nucleotides 311 to 751 of SEQ ID NO:1).

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The invention also provides FMCP chimeric or fusion proteins. As used herein, a FMCP "chimeric protein" or "fusion protein" comprises,; a FMCP polypeptide operatively linked to a non-FMCP polypeptide. A "FMCP polypeptide" refers to a polypeptide having an amino acid sequence corresponding to FMCP, whereas a "non-FMCP polypeptide" refers to a polypeptide having an amino acid sequence corresponding to a protein which is not substantially homologous to the FMCP protein, e.g., a protein which is different from the FMCP protein and which is derived from the same or a different organism. Within a FMCP fusion protein the FMCP polypeptide can correspond to all or a portion of a FMCP protein. In a preferred embodiment, a FMCP fusion protein comprises at least one biologically active portion of a FMCP protein. In another preferred embodiment, a FMCP fusion protein comprises at least two biologically active portions of a FMCP protein. In another preferred embodiment, a FMCP fusion protein comprises at least three biologically active portions of a FMCP protein. Within the fusion protein, the term "operatively linked" is intended to indicate that the FMCP polypeptide and the non-FMCP polypeptide are fused in-frame to each other. The non-FMCP polypeptide can be fused to the N-terminus or C-terminus of the FMCP polypeptide.

For example, in one embodiment a FMCP fusion protein comprises a FMCP follistatin cystein-rich domain domain operably linked to the extracellular domain of a second protein known to be involved in cytokine activity. Such fusion proteins can be further utilized in screening assays for compounds which modulate FMCP activity (such assays are described in detail below).

In yet another embodiment, the fusion protein is a GST-FMCP fusion protein in which the FMCP sequences are fused to the C-terminus of the GST sequences. Such fusion proteins can facilitate the purification of recombinant FMCP.

In another embodiment, the fusion protein is a FMCP protein containing a heterologous signal sequence at its N-terminus. For example, the native FMCP signal sequence (i.e, about amino acids 1 to 26 of SEQ ID NO:2) can be removed and replaced with a signal sequence from another protein. In certain host cells (e.g., mammalian host cells), expression and/or secretion of FMCP can be increased through use of a heterologous signal sequence.

In yet another embodiment, the fusion protein is a FMCP-immunoglobulin fusion protein in which the FMCP sequences comprising primarily the follistatin cysteine-rich domains are fused to sequences derived from a member of the immunoglobulin protein family. The FMCP-immunoglobulin fusion proteins of the invention can be incorporated into pharmaceutical compositions and administered to a subject to inhibit an interaction between a FMCP ligand and a FMCP protein on the surface of a cell, to thereby suppress FMCP-mediated signal transduction in vivo. The FMCP-immunoglobulin fusion proteins can be used to affect the bioavailability of a FMCP cognate ligand. Inhibition of the FMCP ligand/FMCP interaction may be useful therapeutically for both the treatment of proliferative and differentiative disorders, as well as modulating (e.g. promoting or inhibiting) cell survival. Moreover, the FMCP-immunoglobulin fusion proteins of the invention can be used as immunogens to produce anti-FMCP antibodies in a subject, to purify FMCP ligands and in screening assays to identify molecules which inhibit the interaction of FMCP with a FMCP ligand.

Preferably, a FMCP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A FMCP-encoding nucleic acid can be cloned into such an expression vector such that the fusion moiety is linked in-frame to the FMCP protein.

The present invention also pertains to variants of the FMCP proteins which function as either FMCP agonists (mimetics) or as FMCP antagonists. Variants of the FMCP protein can be generated by mutagenesis, e.g., discrete point mutation or truncation of the FMCP protein. An agonist of the FMCP protein can retain substantially the same, or a subset, of the biological activities of the naturally occurring form of the FMCP protein. An antagonist of the FMCP protein can inhibit one or more of the activities of the naturally occurring form of the FMCP protein by, for example, competitively binding to a downstream or upstream member of a cellular signaling cascade which includes the FMCP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the FMCP proteins.

In one, variants of the FMCP protein which function as either FMCP agonists (mimetics) or as FMCP antagonists can be identified by screening combinatorial libraries of mutants, e.g., truncation mutants, of the FMCP protein for FMCP protein agonist or antagonist activity. In one embodiment, a variegated library of FMCP variants is generated by combinatorial mutagenesis at the nucleic acid level and is encoded by a variegated gene library. A variegated library of FMCP variants can be produced by, for example, enzymatically ligating a mixture of synthetic oligonucleotides into gene sequences such that a degenerate set of potential FMCP sequences is expressible as individual polypeptides, or alternatively, as a set of larger fusion proteins (e.g., for phage display) containing the set of FMCP sequences therein. There are a variety of methods which can be used to produce libraries of potential FMCP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FMCP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the FMCP protein coding sequence can be used to generate a variegated population of FMCP fragments for screening and subsequent selection of variants of a FMCP protein. In one embodiment, a library of coding sequence fragments can be generated by treating a double stranded PCR fragment of a FMCP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the FMCP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FMCP proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify FMCP variants (Arkin and Yourvan (1992) *PNAS* 89:7811–7815; Delgrave et al. (1993) *Protein Engineering* 6(3):327–33 1).

In one embodiment, cell based assays can be exploited to analyze a variegated FMCP library. For example, a library of expression vectors can be transfected into a cell line which ordinarily responds to a particular cytokine in a FMCP-dependent manner. The transfected cells are then contacted with the cytokine and the effect of expression of the mutant on signaling by the cytokine can be detected, e.g. by measuring NF-κB activity or cell survival. Plasmid DNA can then be recovered from the cells which score for inhibition, or alternatively, potentiation of cytokine induction, and the individual clones further characterized.

An isolated FMCP protein, or a portion or fragment thereof, can be used as an immunogen to generate antibodies that bind FMCP using standard techniques for polyclonal and monoclonal antibody preparation. The full-length FMCP protein can be used or, alternatively, the invention provides antigenic peptide fragments of FMCP for use as immunogens. The antigenic peptide of FMCP comprises at least 8 amino acid residues of the amino acid sequence shown in SEQ ID NO:2 and encompasses an epitope of FMCP such that an antibody raised against the peptide forms a specific immune complex with FMCP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of FMCP that are located on the surface of the protein, e.g., hydrophilic regions. A hydrophobicity analysis of the human FMCP protein sequence indicates that the regions between amino acids 135–175 and 240–260 are particularly hydrophilic and, therefore, are likely to encode surface residues useful for targeting antibody production.

A FMCP immunogen typically is used to prepare antibodies by immunizing a suitable subject, (e.g., rabbit, goat, mouse or other mammal) with the immunogen. An appropriate immunogenic preparation can contain, for example, recombinantly expressed FMCP protein or a chemically synthesized FMCP polypeptide. The preparation can further include an adjuvant, such as Freund's complete or incomplete adjuvant, or similar immunostimulatory agent. Immunization of a suitable subject with an immunogenic FMCP preparation induces a polyclonal anti-FMCP antibody response.

Accordingly, another aspect of the invention pertains to anti-FMCP antibodies. The term "antibody" as used herein refers to immunoglobulin molecules and immunologically active portions of immunoglobulin molecules, i.e., molecules that contain an antigen binding site which specifically binds (immunoreacts with) an antigen, such as FMCP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind FMCP. The term "monoclonal antibody" or "monoclonal antibody composition", as used herein, refers to a population of antibody molecules that contain only one species of an antigen binding site capable of immunoreacting with a particular epitope of FMCP. A monoclonal antibody composition thus typically displays a single binding affinity for a particular FMCP protein with which it immunoreacts.

Polyclonal anti-FMCP antibodies can be prepared as described above by immunizing a suitable subject with a FMCP immunogen. The anti-FMCP antibody titer in the immunized subject can be monitored over time by standard techniques, such as with an enzyme linked immunosorbent assay (ELISA) using immobilized FMCP. If desired, the antibody molecules directed against FMCP can be isolated from the mammal (e.g., from the blood) and further purified by well known techniques, such as protein A chromatography to obtain the IgG fraction. At an appropriate time after immunization, e.g., when the anti-FMCP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem*.255:498–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genel.* 3:231–36). Briefly, an immortal cell line (typically a myeloma) is fused to lymphocytes (typically splenocytes) from a mammal immunized with a FMCP immunogen as described above, and the culture supernatants of the resulting hybridoma cells are screened to identify a hybridoma producing a monoclonal antibody that binds FMCP.

Any of the many well known protocols used for fusing lymphocytes and immortalized cell lines can be applied for the purpose of generating an anti-FMCP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of he present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind FMCP, e.g., using a standard ELISA assay.

Alternative to preparing monoclonal antibody-secreting hybridomas, a monoclonal anti-FMCP antibody can be identified and isolated by screening a recombinant combinatorial immunoglobulin library (e.g., an antibody phage display library) with FMCP to thereby isolate immunoglobulin library members that bind FMCP. Kits for generating and screening phage display libraries are commercially available (e.g., the Pharmacia *Recombinant Phage Antibody System*, Catalog No. 27-9400-01; and the Stratagene *SurfZAP™Phage Display Kit.*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-FMCP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-FMCP antibody (e.g., monoclonal antibody) can be used to isolate FMCP by standard techniques, such as affinity chromatography or immunoprecipitation. An anti-FMCP antibody can facilitate the purification of natural FMCP from cells and of recombinantly produced FMCP expressed in host cells. Moreover, an anti-FMCP antibody can be used to detect FMCP protein (e.g., in a cellular lysate or cell supernatant) in order to evaluate the abundance and pattern of expression of the FMCP protein. Anti-FMCP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding FMCP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby be replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FMCP proteins, mutant forms of FMCP, fusion proteins, etc.).

The recombinant expression vectors of the invention can be designed for expression of FMCP in prokaryotic or eukaryotic cells. For example, FMCP can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET I d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the FMCP expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, FMCP can be expressed in insect cel Is using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to FMCP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, FMCP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding FMCP or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) FMCP protein. Accordingly, the invention further provides methods for producing FMCP protein using the host cells of the invention. In one embodiment, the method comprises culturing the host cell of invention (into which a recombinant expression vector encoding FMCP has been introduced) in a suitable medium such that FMCP protein is produced. In another embodiment, the method further comprises isolating FMCP from the medium or the host cell.

The host cells of the invention can also be used to produce nonhuman transgenic animals. For example, in one embodiment, a host cell of the invention is a fertilized oocyte or an embryonic stem cell into which FMCP-coding sequences have been introduced. Such host cells can then be used to create non-human transgenic animals in which exogenous FMCP sequences have been introduced into their genome or homologous recombinant animals in which endogenous FMCP sequences have been altered. Such animals are useful for studying the function and/or activity of FMCP and for identifying and/or evaluating modulators of FMCP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FMCP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing FMCP-encoding nucleic acid into the male pronuclei of a fertilized oocyte, e.g., by microinjection, retroviral infection, and allowing the oocyte to develop in a pseudopregnant female foster animal. The human FMCP cDNA sequence of SEQ ID NO:1, SEQ ID NO:3, or the nucleotide sequence of the DNA insert of the plasmid deposited with ATCC as Accession Number 98546 can be introduced as a transgene into the genome of a non-human animal. Alternatively, a nonhuman homologue of the human FMCP gene, such as a mouse FMCP gene, can be isolated based on hybridization to the human FMCP cDNA (described further in subsection I above) and used as a transgene. Intronic sequences and polyadenylation signals can also be included in the transgene to increase the efficiency of expression of the transgene. A tissue-specific regulatory sequence(s) can be operably linked to the FMCP transgene to direct expression of FMCP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the FMCP transgene in its genome and/or expression of FMCP mRNA in tissues or cells of the animals. A transgenic founder animal can then be used to breed additional animals carrying the transgene. Moreover, transgenic animals carrying a transgene encoding FMCP can further be bred to other transgenic animals carrying other transgenes.

To create a homologous recombinant animal, a vector is prepared which contains at least a portion of a FMCP gene into which a deletion, addition or substitution has been introduced to thereby alter, e.g., functionally disrupt, the FMCP gene. The FMCP gene can be a human gene (e.g., the cDNA of SEQ ID NO:1, SEQ ID NO:3, or the nucleotide sequence of the DNA insert of the plasmid deposited with ATCC as Accession Number 98546), but more preferably, is a non-human homologue of a human FMCP gene. For example, a mouse homologue of human FMCP gene of SEQ ID NO:1, SEQ ID NO:3, or the nucleotide sequence of the DNA insert of the plasmid deposited with ATCC as Accession Number 98546 can be used to construct a homologous recombination vector suitable for altering an endogenous FMCP gene in the mouse genome. In a preferred embodiment, the vector is designed such that, upon homologous recombination, the endogenous FMCP gene is functionally disrupted (i.e., no longer encodes a functional protein; also referred to as a "knock out" vector). Alternatively, the vector can be designed such that, upon homologous recombination, the endogenous FMCP gene is mutated or otherwise altered but still encodes functional protein (e.g., the upstream regulatory region can be altered to thereby alter the expression of the endogenous FMCP protein). In the homologous recombination vector, the altered portion of the FMCP gene is flanked at its 5' and 3' ends by additional nucleic acid of the FMCP gene to allow for homologous recombination to occur between the exogenous FMCP gene carried by the vector and an endogenous FMCP gene in an embryonic stem cell. The additional flanking FMCP nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced FMCP gene has homologously recombined with the endogenous FMCP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) PNAS 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut. I. et al. (1997) *Nature* 385:810– 813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The FMCP nucleic acid molecules, FMCP proteins, and anti-FMCP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as elhylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a FMCP protein or anti-FMCP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesteirs, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantily of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

Proteins containing follistatin domains are known to bind TGF-β superfamily members. TGF-β superfamily members are multifunctional cytokines which modulate a number of functions. The nucleic acid molecules, proteins, protein homologues, and antibodies described herein which include follistatin-related domains, therefore, can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). As described herein, in one embodiment, a FMCP protein of the invention has the ability to bind and inactivate TGF-β family members. A FMCP protein interacts with other cellular proteins and can thus be used to (i) modulation of TGF-β-related protein activity; (ii) regulation of cellular proliferation; (iii) regulation of of cellular differentiation; and (iv) regulation of cell survival. The isolated nucleic acid molecules of the invention can be used to express FMCP protein (e.g., via a recombinant expression vector in a host cell in gene therapy applications), to detect FMCP mRNA (e.g., in a biological sample) or a genetic lesion in a FMCP gene, and to modulate FMCP activity, as described further below. In addition, the FMCP proteins can be used to screen drugs or compounds which modulate the FMCP activity or expression as well as to treat disorders characterized by insufficient or excessive production of FMCP protein or production of FMCP protein forms which have decreased or aberrant activity compared to FMCP wild type protein (e.g. proliferative disorders such as cancer or preclampsia). In addition, the anti-FMCP antibodies of the invention can be used to detect and isolate FMCP proteins and modulate FMCP activity.

This invention further pertains to novel agents identified by the above described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to FMCP proteins or have a stimulatory or inhibitory effect on, for example, FMCP expression or FMCP activity.

In one embodiment, the invention provides assays for screening candidate or test compounds which bind to or modulate the activity of the membrane-bound form of a FMCP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a membrane-bound form of FMCP protein, or a biologically active portion thereof, on the cell surface is contacted with a test compound and the ability of the test compound to bind to a FMCP protein determined. The cell for example, can of mammalian origin or a yeast cell. Determining the ability of the test compound to bind to the FMCP protein can be accomplished, for example, by coupling the test compound with a radioisotope or enzymatic label such that binding of the test compound to the FMCP protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of FMCP protein, or a biologically active portion thereof, on the cell surface with a known compound which binds FMCP to form an assay mixture, contacting the assay mixture with a test compound, and determining the ability of the test compound to interact with a FMCP protein, wherein determining the ability of the test compound to interact with a FMCP protein comprises determining the ability of the test compound to preferentially bind to FMCP or a biologically active portion thereof as compared to the known compound.

In another embodiment, an assay is a cell-based assay comprising contacting a cell expressing a membrane-bound form of FMCP protein, or a biologically active portion thereof, on the cell surface with a test compound and determining the ability of the test compound to modulate (e.g. stimulate or inhibit) the activity of the FMCP protein or biologically active portion thereof. Determining the ability of the test compound to modulate the activity of FMCP or a biologically active portion thereof can be accomplished, for example, by determining the ability of the FMCP protein to bind to or interact with a FMCP target molecule. As used herein, a "target molecule" is a molecule with which a FMCP protein binds or interacts in nature, for example, a molecule on the surface of a cell which expresses a FMCP protein, a molecule on the surface of a second cell, a molecule in the extracellular milieu, a molecule associated with the internal surface of a cell membrane or a cytoplasmic molecule. A FMCP target molecule can be a non-FMCP molecule or a FMCP protein or polypeptide of the present invention. In one embodiment, a FMCP target molecule is a component of a signal transduction pathway which facilitates transduction of an extracellular signal (e.g. a signal generated by binding of a compound to a membrane-bound FMCP molecule) through the cell membrane and into the cell. The target, for example, can be a second intercellular protein which has catalytic activity or a protein which facilitates the association of downstream signaling molecules with FMCP.

Determining the ability of the FMCP protein to bind to or interact with a FMCP target molecule can be accomplished by one of the methods; described above for determining direct binding. In a preferred embodiment, determining the ability of the FMCP protein to bind to or interact with a FMCP target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a FMCP-responsive regulatory element operatively linked to a nucleic acid encoding a detectable marker, e.g. luciferase), or detecting a cellular response, for example, cell survival, cellular differentiation, or cell proliferation.

In yet another embodiment, an assay of the present invention is a cell-free assay comprising contacting a FMCP protein or biologically active portion thereof with a test compound and determining the ability of the test compound to bind to the FMCP protein or biologically active portion thereof. Binding of the test compound to the FMCP protein can be determined either directly or indirectly as described above. In a preferred embodiment, the assay comprises contacting the FMCP protein or biologically active portion thereof with a known compound which binds FMCP to form an assay mixture, contacting the assay mixture with a test compound, and determining the ability of the test compound to interact with a FMCP protein, wherein determining the ability of the test compound to interact with a FMCP protein comprises determining the ability of the test compound to preferentially bind to FMCP or biologically active portion thereof as compared to the known compound.

In another embodiment, an assay is a cell-free assay comprising contacting FMCP protein or biologically active portion thereof with a test compound and determining the ability of the test compound to modulate (e.g. stimulate or inhibit) the activity of the FMCP protein or biologically active portion thereof. Determining the ability of the test compound to modulate the activity of FMCP can be accomplished, for example, by determining the ability of the FMCP protein to bind to a FMCP target molecule by one of the methods described above for determining direct binding. In an alternative embodiment, determining the ability of the test compound to modulate the activity of FMCP can be accomplished by determining the ability of the FMCP protein further modulate a FMCP target molecule. For example, the catalytic/enzymatic activity of the target molecule on an appropriate substrate can be determined as previously described.

In yet another embodiment, the cell-free assay comprises contacting the FMCP protein or biologically active portion thereof with a known compound which binds FMCP to form an assay mixture, contacting the assay mixture with a test compound, and determining the ability of the test compound to interact with a FMCP protein, wherein determining the ability of the test compound to interact with a FMCP protein comprises determining the ability of the FMCP protein to preferentially bind to or modulate the activity of a FMCP target molecule.

The cell-free assays of the present invention are amenable to use of both the soluble form or the membrane-bound form of FMCP. In the case of cell-free assays comprising the membrane-bound form of FMCP, it may be desirable to utilize a solubilizing such that the membrane-bound form of FMCP is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either FMCP or its target molecule to facilitate separation of complexed from uncomplexed forms of one or both of the proteins, as well as to accommodate automation of the assay. Binding of a test compound to FMCP, or interaction of FMCP with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/FMCP fusion proteins or glutathione-S-transferase/target fusion proteins can be adsorbed onto glutathione sepharose beads (Sigma Chemical, St. Louis, MO) or glutathione derivatized microtitre plates, which are then combined with the test compound or the test compound and either the non-adsorbed target protein or FMCP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of FMCP binding or activity determined using standard techniques.

Other techniques for immobilizing proteins on matrices can also be used in the screening assays of the invention. For example, either FMCP or its target molecule can be immobilized utilizing conjugation of biotin and streptavidin. Biotinylated FMCP or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with FMCP or target molecules but which do not interfere with binding of the FMCP protein to its target molecule can be derivatized to the wells of the plate, and unbound target or FMCP trapped in the wells by antibody conjugation. Methods for detecting such complexes, in addition to those described above for the GST-immobilized complexes, include immunodetection of complexes using antibodies reactive with the FMCP or target molecule, as well as enzyme-linked assays which rely on detecting an enzymatic activity associated with the FMCP or target molecule.

In another embodiment, modulators of FMCP expression are identified in a method wherein a cell is contacted with a candidate compound and the expression of FMCP mRNA or protein in the cell is determined. The level of expression of FMCP mRNA or protein in the presence of the candidate compound is compared to the level of expression of FMCP mRNA or protein in the absence of the candidate compound. The candidate compound can then be identified as a modulator of FMCP expression based on this comparison. For example, when expression of FMCP mRNA or protein is greater (statistically significantly greater) in the presence of the candidate compound than in its absence, the candidate compound is identified as a stimulator of FMCP mRNA or protein expression. Alternatively, when expression of FMCP mRNA or protein is less (statistically significantly less) in the presence of the candidate compound than in its absence, the candidate compound is identified as an inhibitor of FMCP mRNA or protein expression. The level of FMCP mRNA or protein expression in the cells can be determined by methods described herein for detecting FMCP mRNA or protein.

In yet another aspect of the invention, the FMCP proteins can be used as "bait proteins" in a two-hybrid assay or three hybrid assay (see, e.g., U.S. Pat. No. 5,283,317; Zervos et al. (1993) Cell 72:223–232; Madura el al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with FMCP ("FMCP-binding proteins" or "FMCP-bp") and modulate FMCP activity. Such FMCP-binding proteins are also likely to be involved in the propagation of signals by the FMCP proteins as, for example, upstream or downstream elements of the FMCP pathway.

The two-hybrid system is based on the modular nature of most transcription factors, which consist of separable DNA-binding and activation domains. Briefly, the assay utilizes two different DNA constructs. In one construct, the gene that codes for FMCP is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a FMCP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with FMCP.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the FMCP, sequences, described herein, can be used to map the location of the FMCP genes, respectively, on a chromosome. The mapping of the FMCP sequences to chromosomes is an important first step in correlating these sequences with genes associated with disease.

Briefly, FMCP genes can be mapped to chromosomes by preparing PCR primers (preferably 15–25 bp in length) from the FMCP sequences. Computer analysis of the FMCP, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the FMCP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells; cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the FMCP sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA. sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the FMCP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The FMCP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the FMCP sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The FMCP sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from FMCP sequences described herein is used to generate a unique identification database for an individual, those same reagents can later be used to identify tissue from that individual. Using the unique identification database, positive identification of the individual, living or dead, can be made from extremely small tissue samples.

3. Use of Partial FMCP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NOs:1, 5, and 10 are particularly appropriate for this use as greater numbers of polymorphisms occur in the noncoding regions, making it easier to differentiate individuals using this technique. Examples of polynucleotide reagents include the FMCP sequences or portions thereof, e.g., fragments derived from the noncoding regions of SEQ ID NO:1, having a length of at least 20 bases, preferably at least 30 bases.

The FMCP sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such FMCP probes can be used to identify tissue by species and/or by organ type.

In a similar fashion, these reagents, e.g., FMCP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining FMCP protein and/or nucleic acid expression as well as FMCP activity, in the context of a biological sample (e.g., blood, serum, cells, tissue) to thereby determine whether an individual is afflicted with a disease or disorder, or is at risk of developing a disorder, associated with aberrant FMCP expression or activity. The invention also provides for prognostic (or predictive) assay s for determining whether an individual is at risk of developing a disorder associated with FMCP protein, nucleic acid expression or activity. For example, mutations in a FMCP gene can be assayed in a biological sample. Such assays can be used for prognostic or predictive purpose to thereby phophylactically treat an individual prior to the onset of a disorder characterized by or associated with FMCP protein, nucleic acid expression or activity.

Another aspect of the invention provides methods for determining FMCP protein, nucleic acid expression or FMCP activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of FMCP in clinical trials.

These and other agents are described in further detail in the following sections.

1 Diagnostic Assays

An exemplary method for detecting the presence or absence of FMCP in a biological sample involves obtaining a biological sample from a test subject and contacting the biological sample with a compound or an agent capable of detecting FMCP protein or nucleic acid (e.g., mRNA, genomic DNA) that encodes FMCP protein such that the presence of FMCP is detected in the biological sample. A preferred agent for detecting FMCP mRNA or genomic DNA is a labeled nucleic acid probe capable of hybridizing to FMCP mRNA or genomic DNA. The nucleic acid probe can be, for example, a full-length FMCP nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to FMCP mRNA or genomic DNA. Other suitable probes for use in the diagnostic assays of the invention are described herein.

A preferred agent for detecting FMCP protein is an antibody capable of binding to FMCP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect FMCP mRNA, protein, or genomic DNA in a biological sample in vitro as well as in vivo. For example, in vitro techniques for detection of FMCP mRNA include Northern hybridizations and in situ hybridizations. In vitro techniques for detection of FMCP protein include enzyme linked immunosorbent assays (ELISAs), Western blots, immunoprecipitations and immunofluorescence. In vitro techniques for detection of FMCP genomic DNA include Southern hybridizations. Furthermore, in vivo techniques for detection of FMCP protein include introducing into a subject a labeled anti-FMCP antibody. For example, the antibody can be labeled with a radioactive marker whose presence and location in a subject can be detected by standard imaging techniques.

In one embodiment, the biological sample contains protein molecules from the test subject. Alternatiavely, the biological sample can contain mRNA molecules from the test subject or genomic DNA molecules from the test subject. A preferred biological sample is a peripheral blood leukocyte sample isolated by conventional means from a subject.

In another emodiment, the methods further involve obtaining a control biological sample from a control subject, contacting the control sample with a compound or agent capable of detecting FMCP protein, mRNA, or genomic DNA, such that the presence of FMCP protein, mRNA or genomic DNA is detected in the biological sample, and comparing the presence of FMCP protein, mRNA or genomic DNA in the control sample with the presence of FMCP protein, mRNA or genomic DNA in the test sample.

The invention also encompasses kits for detecting the presence of FMCP in a biological sample. For example, the kit can comprise a labeled compound or agent capable of detecting FMCP protein or mRNA in a biological sample; means for determining the amount of FMCP in the sample; and means for comparing the amount of FMCP in the sample with a standard. The compound or agent can be packaged in a suitable container. The kit can further comprise instructions for using the kit to detect FMCP protein or nucleic acid.

2. Prognostic Assays

The diagnostic method s described herein can furthermore be utilized to identify subjects having or at risk of developing a disease or disorder associated with aberrant FMCP expression or activity. For example, the assays described herein, such as the preceding diagnostic assays or the following assays, can be utilized to identify a subject having or at risk of developing a disorder associated with FMCP protein, nucleic acid expression or activity such as cancer or fibrotic disorders. Alternatively, the prognostic assays can be utilized to identify a subject having or at risk for developing a disease or disorder. Thus, the present invention provide s a method for identifying a disease or disorder associated with aberrant FMCP expression or activity in which a test sample is obtained from a subject an d FMCP protein or nucleic acid (e.g, mRNA, genomic DNA) is detected, wherein the presence of FMCP protein or nucleic acid is diagnostic for a subject having or at risk of developing a disease or disorder associated with aberrant FMCP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein , peptide, nucleic acid, small molecule, or other drug candidate) to treat a disease or disorder associated with aberrant FMCP expression or activity. For example, such methods can be used to determine whether a subject can be effectively treated with an agent for a disorder, such as cancer or pre-clampsia. Thus, the present invention provides methods for determining whether a subject can be effectively treated with an agent for a disorder associated with aberrant FMCP expression or activity in which a test sample is obtained and FMCP protein or nucleic acid is detected (e.g., wherein the presence of FMCP protein or nucleic acid is diagnostic for a subject that can be administered the agent to treat a disorder associated with aberrant FMCP expression or activity.)

The methods of the invention can also be used to detect genetic lesions in a FMCP gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a FMCP-protein, or the mis-expression of the FMCP gene. For example, such genetic lesions can be detected by ascertaining the existence of at least one of 1) a deletion of one or more nucleotides from a FMCP gene; 2) an addition of one or more nucleotides to a FMCP gene; 3) a substitution of one or more nucleotides of a FMCP gene, 4) a chromosomal rearrangement of a FMCP gene; 5) an alteration in the level of a messenger RNA transcript of a FMCP gene, 6) aberrant modification of a FMCP gene, such as of the methylation pattern of the genomic DNA, 7) the presence of a non-wild type splicing pattern of a messenger RNA transcript of a FMCP gene, 8) a non-wild type level of a FMCP-protein, 9) allelic loss of a FMCP gene, and 10) inappropriate post-translational modification of a FMCP-protein. As described herein, there are a large number of assay techniques known in the art which can be used for detecting lesions in a FMCP gene. A preferred biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the FMCP-gene (see Abravaya et al. (1995) *Nucleic Acids Res*.23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a FMCP gene under conditions such that hybridization and amplification of the FMCP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, *Proc. Natl. Acad. Sci. USA* 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a FMCP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in FMCP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in FMCP can be identified in two dimensional arrays containing light-generated DNA probes as described. in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the FMCP gene and detect mutations by comparing the sequence of the sample FMCP with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the FMCP gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type FMCP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in FMCP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a FMCP sequence, e.g., a wild-type FMCP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in FMCP genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) *Genet Anal Tech Appl* 9:73–79). Single-stranded DNA fragments of sample and control FMCP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site b y looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a FMCP gene.

Furthermore, any cell type or tissue, preferably peripheral blood leukocytes, in which FMCP is expressed may be utilized in the prognostic assays described herein.

3. Pharmacogenomics

Agents, or modulators which have a stimulatory or inhibitory effect on FMCP activity (e.g., FMCP gene expression) as identified by a screening assay described herein can be administered to individuals to treat (prophylactically or therapeutically) disorders (e.g, cancer or gestational disorders) associated with aberrant FMCP activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of FMCP protein, expression of FMCP nucleic acid, or mutation content of FMCP genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, M., *Clin Exp Pharmacol Physiol,* 1996, 23(10–11):983–985 and Linder, M. W., *Clin Chem,* 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of FMCP protein, expression of FMCP nucleic acid, or mutation content of FMCP genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a FMCP modulator, such as a modulator identified by one of the exemplary screening assays described herein.

4. Monitoring of Effects During Clinical Trials

Monitoring the influence of agents (e.g., drugs, compounds) on the expression or activity of FMCP (e.g., the ability to modulate aberrent cell proliferation and/or differentiation) can be applied not only in basic drug screening, but also in clinical trials. For example, the effectiveness of an agent determined by a screening assay as described herein to increase FMCP gene expression, protein levels, or upregulate FMCP activity, can be monitored in clinical trails of subjects exhibiting decreased FMCP gene expression, protein levels, or downregulated FMCP activity. Alternatively, the effectiveness of an agent determined by a screening assay to decrease FMCP gene expression, protein levels, or downregulate FMCP activity, can be monitored in clinical trails of subjects exhibiting increased FMCP gene expression, protein levels, or upregulated FMCP activity. In such clinical trials, the expression or activity of FMCP and, preferably, other genes that have been implicated in, for example, a cellular proliferation disorder can be used as a "read out" or markers of the immune responsiveness of a particular cell.

For example, and not by way of limitation, genes, including FMCP, that are modulated in cells by treatment with an agent (e.g., compound, drug or small molecule) which modulates FMCP activity (e.g., identified in a screening assay as described herein) can be identified. Thus, to study the effect of agents on cellular proliferation disorders, for example, in a clinical trial, cells can be isolated and RNA prepared and analyzed for the levels of expression of FMCP and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of FMCP or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a FMCP protein, mRNA, or genomic DNA in the preadministration sample; (iii) obtaining one or more post-administration samples from the subject; (iv) detecting the level of expression or activity of the FMCP protein, mRNA, or genomic DNA in the post-administration samples; (v) comparing the level of expression or activity of the FMCP protein, mRNA, or genomic DNA in the pre-administration sample with the FMCP protein, mRNA, or genomic DNA in the post administration sample or samples; and (vi) altering the administration of the agent to the subject accordingly. For example, increased administration of the agent may be desirable to increase the expression or activity of FMCP to higher levels than detected, i.e., to increase the effectiveness of the agent. Alternatively, decreased administration of the agent may be desirable to decrease expression or activity of FMCP to lower levels than detected, i.e. to decrease the effectiveness of the agent.

C. Methods of Treatment:

The present invention provides for both prophylactic and therapeutic methods of treating a subject at risk of (or susceptible to) a disorder or having a disorder associated with aberrant FMCP expression or activity.

1. Prophylactic Methods

In one aspect, the invention provides a method for preventing in a subject, a disease or condition associated with an aberrant FMCP expression or activity, by administering to the subject an agent which modulates FMCP expression or at least one FMCP activity. Subjects at risk for a disease which is caused or contributed to by aberrant FMCP expression or activity can be identified by, for example, any or a combination of diagnostic or prognostic assays as described herein. Administration of a phophylactic agent can occur prior to the manifestation of symptoms characteristic of the FMCP aberrancy, such that a disease or disorder is prevented or, alternatively, delayed in its progression. Depending on the type of FMCP aberrancy, for example, a FMCP agonist or FMCP antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating FMCP expression or activity for therapeutic purposes. The modulatory method of the invention involves contacting a cell with an agent that modulates one or more of the activities of FMCP protein activity associated with the cell. An agent that modulates FMCP protein activity can be an agent as described herein, such as a nucleic acid or a protein, a naturally-occurring cognate ligand of a FMCP protein, a peptide, a FMCP peptidomimetic, or other small molecule. In one embodiment, the agent stimulates one or more FMCP protein activity. Examples of such stimulatory agents include active FMCP protein and a nucleic acid molecule encoding FMCP that has been introduced into the cell. In another embodiment, the agent inhibits one or more FMCP protein activity. Examples of such inhibitory agents include antisense FMCP nucleic acid molecules and anti-FMCP antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a FMCP protein or nucleic acid molecule. In one embodiment, the method involves administering an agent (e.g., an agent identified by a screening assay described herein), or combination of agents that modulates (e.g., upregulates or downregulates) FMCP expression or activity. In another embodiment, the method involves administering a FMCP protein or nucleic acid molecule as therapy to compensate for reduced or aberrant FMCP expression or activity.

Stimulation of FMCP activity is desirable in situations in which FMCP is abnormally downregulated and/or in which increased FMCP activity is likely to have a beneficial effect. One example of such a situation is where a subject has a disorder characterized by aberrant cell proliferation and/or differentiation (e.g., cancer). Another example of such a situation is where the subject has a gestational disease (e.g., pre-clampsia).

This invention is further illustrated by the following examples which should not be construed as limiting. The contents of all references, patents and published patent applications cited throughout this application are hereby incorporated by reference.

EXAMPLES

Example 1

Isolation And Characterization Of Human FMCP cDNAs

In this example, the isolation of the genes encoding human FMCP is described.

Isolation of FMCP

Human coronary artery smooth muscle cells (obtained from Clonetics Corporation; San Diego, Calif.) were expanded in culture with Smooth Muscle Growth Media (SmGM; Clonetics) according to the recommendations of the supplier. When the cells reached 80% confluence, they were stimulated with SMGM, tumor necrosis factor (TNF −10 ng/ml) and cycloheximide (CHI; 40 micrograms/ml) for 4 hours. Total RNA was isolated using the RNeasy Midi Kit (Qiagen; Chatsworth, Calif.), and the poly A+ fraction was further purified using Oligotex beads (Qiagen)

Three micrograms of poly A+ RNA were used to synthesize a cDNA library using the Superscript cDNA Synthesis kit (Gibco BRL; Gaithersburg, Md.). Complementary DNA was directionally cloned into the expression plasmid pMET7 using the SalI and NotI sites in the polylinker to construct a plasmid library. Transformants were picked and grown up for single-pass sequencing. Additionally, coronary artery smooth muscle cDNA was ligated into the SalI/NotI sites of the ZipLox vector (Gibco BRL) for construction of a lambda phage cDNA library.

FMCP was identified using Sequence Explorer®, a sequence analysis tool that integrates the output from high-throughput sequencing projects with automated BLAST searches of the protein, nucleic and EST databases. The original first pass sequence of the FMCP clone showed homology to human follistatin using the BLASTX program, which translates a nucleic acid sequence in all six frames and compares it against available protein databases. This clone was then grown up for full sequencing to confirm the homology to follistatin.

Example 2

Distribution Of FMCP mRNA Human Tissues

The expression of FMCP was analyzed using Northern blot hybridization. A 956 base pair (bp) DNA fragment (the SalI/BamHI fragment containing the 5' end of the FMCP cDNA) was used as a probe. The DNA was radioactively labeled with $^{32}$P-dCTP using the Prime-It kit (Stratagene, La Jolla, Calif.) according to the instructions of the supplier. Filters containing human mRNA (MTNI and MTNII from Clontech, Palo Alto, Calif.) were probed in ExpressHyb hybridization solution (Clontech) and washed at high stringency according to manufacturer's recommendations.

FMCP is expressed as an ~2.5 kilobase (kb) transcript in a wide variety of tissues (heart, placenta, lung, liver, skeletal muscle, kidney, pancreas, spleen, prostate, testis, ovaries, small intestine, and colon), with the highest levels found in the placenta, testis and heart. This is in good agreement with the size of the cDNA clone isolated. In addition, a smaller transcript of ~1.4 kb is also seen in heart, placenta, lung, kidney and testis.

Example 3

Characterization Of FMCP Proteins

In this example, the predicted amino acid sequences of the human FMCP proteins were compared to amino acid sequences of known proteins and various motifs were identified. In addition, the molecular weight of the human FMCP proteins was predicted.

The human FMCP cDNA encodes a protein of 263 amino acids (predicted MW of 25 kDa, not including post-translational modifications). is signal peptide is predicted to exist from aa 1–26, using the prediction program SIGNALP (Henrik Nielsen, Jacob Engelbrecht, Soren Brunak and Gunnar von Heijne "Identification of prokaryotic and eukaryotic signal peptides and prediction of their cleavage sites." (1997) Protein Engineering 10, 1–6). The human protein appears to be secreted or retained in an intracellular compartment and there is no evidence of a transmembrane domain.

Alignment of the human FMCP protein with the human follistatin protein using the Wisconsin GCG sequence alignment program GAP, reveals that FMCP is 43% identical and 61% similar to the human follistatin gene. Similarly, when FMCP is aligned with the human follistatin-related gene (hFRP) (Swiss Prot Q12841) using GAP, it show a 24% identity and 48% similarity to hFRP.

Example 4

Preparation Of FMCP Protein.

Recombinant FMCP can be produced in a variety of expression systems. For example, the mature FMCP peptide can be expressed as a recombinant glutathione-S-transferase (GST) fusion protein in *E. coli* and the fusion protein can be isolated and characterized. Specifically, as described above, FMCP can be fused to GST and this fusion protein can be expressed in *E. coli* strain PEB199. As FMCP is predicted to be 25 kD and GST is predicted to be 26 kD, the fusion protein is predicted to be 51 kD in molecular weight. Expression of the GST-FMCP fusion protein in PEB199 can be induced with IPTG. The recombinant fusion protein can be purified from crude bacterial lysates of the induced PEB199 strain by affinity chromatography on glutathione beads. Using polyacrylamide gel electrophoretic analysis of the proteins purified from the bacterial lysates, the resultant fusion protein should be 51 kD in size.

Equivalents Those skilled in the art will recognize, or be able to ascertain using no more than routine experimentation, many equivalents to the specific embodiments of the invention described herein. Such equivalents are intended to be encompassed by the following claims.

---

What is claimed:

1. An isolated nucleic acid molecule comprising a nucleotide sequence which encodes an amino acid sequence which is at least 55% identical to the amino acid sequence of SEQ ID NO:2 with or without the signal peptide or an amino acid sequence encoded by the nucleotide sequence of the DNA insert of the plasmid deposited with ATCC as Accession Number 98546.

2. The isolated nucleic acid molecule of claim 1, which comprises a nucleotide sequence which encodes an amino acid sequence which is at least 75% identical to the amino acid sequence of SEQ ID NO:2 with or without the signal peptide or an amino acid sequence encoded by the nucleotide sequence of the DNA insert of the plasmid deposited with ATCC as Accession Number 98546.

3. The isolated nucleic acid molecule of claim 2, which comprises a nucleotide sequence which encodes an amino acid sequence which is at least 85% identical to the amino acid sequence of SEQ ID NO:2 with or without the signal peptide or an amino acid sequence encoded by the nucleotide sequence of the DNA insert of the plasmid deposited with ATCC as Accession Number 98546.

4. The isolated nucleic acid molecule of claim 3, which comprises a nucleotide sequence which encodes an amino acid sequence which is at least 95% identical to the amino acid sequence of SEQ ID NO:2 with or without the signal peptide or an amino acid sequence encoded by the nucleotide sequence of the DNA insert of the plasmid deposited with ATCC as Accession Number 98546.

5. The isolated nucleic acid molecule of claim 1, 2, 3, or 4, wherein the nucleotide sequence encodes a polypeptide comprising an amino acid sequence which is at least 85% identical to a follistatin cysteine-rich domain selected from the group consisting of the follistatin cysteine-rich domain comprising amino acid residues 97 to 167 of SEQ ID NO:2 and the follistatin cysteine-rich domain comprising amino acid residues 171 to 243 of SEQ ID NO:2.

6. The isolated nucleic acid molecule of claim 5, wherein the follistatin cysteine-rich domain comprises amino acid residues 97 to 167 of SEQ ID NO:2.

7. The isolated nucleic acid molecule of claim 5, wherein the follistatin cysteine-rich domain comprises amino acid residues 171 to 243 of SEQ ID NO:2.

8. The isolated nucleic acid molecule of claim 1, 2, 3, or 4, wherein the polypeptide comprises an amino acid sequence which is at least 85% identical to the follistatin cysteine-rich domain comprising amino acid residues 97 to 167 of SEQ ID NO:2 and the follistatin cysteine-rich domain comprising amino acid residues 171 to 243 of SEQ ID NO:2.

9. The isolated nucleic acid molecule of claim 8, wherein the polypeptide comprises the follistatin cysteine-rich domain comprising amino acid residues 97 to 167 of SEQ ID NO:2 and the follistatin cysteine-rich domain comprising amino acid residues 171 to 243 of SEQ ID NO:2.

10. An isolated nucleic acid molecule comprising a nucleotide sequence encoding a polypeptide comprising an amino acid sequence at least about 55% identical to a follistatin-cysteine-rich domain of SEQ ID NO:2.

11. The isolated nucleic acid molecule of claim 10, wherein the amino acid sequence is at least about 65% identical to a follistatin-cysteine-rich domain of SEQ ID NO:2.

12. The isolated nucleic acid molecule of claim 11, wherein the amino acid sequence is at least about 75% identical to a follistatin-cysteine-rich domain of SEQ ID NO:2.

13. The isolated nucleic acid molecule of claim 12, wherein the amino acid sequence is at least about 85% identical to a follistatin-cysteine-rich domain of SEQ ID NO:2.

14. The isolated nucleic acid molecule of claim 10, 11, 12, or 13, wherein the follistatin cysteine-rich domain comprises amino acid residues 97 to 167 of SEQ ID NO:2.

15. The isolated nucleic acid molecule of claim 10, 11, 12, or 13, wherein the follistatin cysteine-rich domain comprises amino acid residues 171 to 243 of SEQ ID NO:2.

16. An isolated nucleic acid molecule comprising a nucleotide sequence which encodes a polypeptide comprising the follistatin cysteine-rich domain comprising amino acid residues 97 to 167 of SEQ ID NO:2 and the follistatin cysteine-rich domain comprising amino acid residues 171 to 243 of SEQ ID NO:2.

17. An isolated nucleic acid molecule comprising a nucleotide sequence which encodes the amino acid sequence of SEQ ID NO:2.

18. An isolated nucleic acid molecule comprising a nucleotide sequence which encodes the amino acid sequence of SEQ ID NO:2 without the signal peptide.

19. An isolated nucleic acid molecule comprising a nucleotide sequence which encodes the amino acid sequence encoded by the nucleotide sequence of the DNA insert of the plasmid deposited with ATCC as Accession Number 98546.

20. An isolated nucleic acid molecule comprising a nucleotide sequence which encodes the mature polypeptide encoded by the nucleotide sequence of the DNA insert of the plasmid deposited with ATCC as Accession Number 98546.

21. An isolated nucleic acid molecule comprising a nucleotide sequence which hybridizes under stringent hybridization conditions to the nucleotide sequence of SEQ ID NO:1, wherein the nucleotide sequence encodes a polypeptide comprising an amino acid sequence which is at least 85% identical to the follistatin cysteine-rich domain comprising amino acid residues 97 to 167 of SEQ ID NO:2 or the follistatin cysteine-rich domain comprising amino acid residues 171 to 243 of SEQ ID NO:2.

22. The isolated nucleic acid molecule of claim 21, wherein the nucleotide sequence encodes a polypeptide comprising the follistatin cysteine-rich domain comprising amino acid residues 97 to 167 of SEQ ID NO:2 or the follistatin cysteine-rich domain comprising amino acid residues 171 to 243 of SEQ ID NO:2.

23. An isolated nucleic acid molecule comprising a nucleotide sequence which hybridizes under stringent hybridization conditions to the nucleotide sequence of SEQ ID NO:3, wherein the nucleotide sequence encodes a polypeptide comprising an amino acid sequence which is at least 85% identical to the follistatin cysteine-rich domain comprising amino acid residues 97 to 167 of SEQ ID NO:2 or the follistatin cysteine-rich domain comprising amino acid residues 171 to 243 of SEQ ID NO:2.

24. The isolated nucleic acid molecule of claim 23, wherein the polypeptide comprises the follistatin cysteine-rich domain comprising amino acid residues 97 to 167 of SEQ ID NO:2 or the follistatin cysteine-rich domain comprising amino acid residues 171 to 243 of SEQ ID NO:2.

25. An isolated nucleic acid molecule comprising a nucleotide sequence which hybridizes under stringent hybridization conditions to the nucleotide sequence of the DNA insert of the plasmid deposited with ATCC as Accession Number 98546, wherein the nucleotide sequence encodes a polypeptide comprising an amino acid sequence which is at least 85% identical to the follistatin cysteine-rich domain comprising amino acid residues 97 to 167 of SEQ ID NO:2 or the follistatin cysteine-rich domain comprising amino acid residues 171 to 243 of SEQ ID NO:2.

26. The isolated nucleic acid molecule of claim 25, wherein the polypeptide comprises the follistatin cysteine-rich domain comprising amino acid residues 97 to 167 of SEQ ID NO:2 or the follistatin cysteine-rich domain comprising amino acid residues 171 to 243 of SEQ ID NO:2.

27. An isolated nucleic acid molecule comprising a nucleotide sequence which hybridizes under stringent hybridization conditions to the nucleotide sequence of SEQ ID NO:1, wherein the nucleotide sequence encodes a polypeptide comprising the follistatin cysteine-rich domain comprising amino acid residues 97 to 167 of SEQ ID NO:2 and the follistatin cysteine-rich domain comprising amino acid residues 171 to 243 of SEQ ID NO:2.

28. An isolated nucleic acid molecule comprising a nucleotide sequence which hybridizes under stringent hybridization conditions to the nucleotide sequence of SEQ ID NO:3, wherein the nucleotide sequence encodes a polypeptide comprising the follistatin cysteine-rich domains comprising amino acid residues 97 to 167 of SEQ ID NO:2 and the follistatin cysteine-rich domain comprising amino acid residues 171 to 243 of SEQ ID NO:2.

29. An isolated nucleic acid molecule comprising a nucleotide sequence which hybridizes under stringent hybridization conditions to the nucleotide sequence of the DNA insert of the plasmid deposited with ATCC as Accession Number 98546, wherein the nucleotide sequence encodes a polypeptide comprising the follistatin cysteine-rich domain comprising amino acid residues 97 to 167 of SEQ ID NO:2 and the follistatin cysteine-rich domain comprising amino acid residues 171 to 243 of SEQ ID NO:2.

30. An isolated nucleic acid molecule which hybridizes under stringent hybridization conditions to a nucleic acid molecule comprising nucleotides 311 to 751 of SEQ ID NO:1 and which encodes a polypeptide comprising the follistatin cysteine-rich domain comprising amino acid residues 97 to 167 of SEQ ID NO:2 or the follistatin cysteine-rich domain comprising amino acid residues 171 to 243 of SEQ ID NO:2.

31. An isolated nucleic acid molecule which hybridizes under stringent hybridization conditions to a nucleic acid molecule comprising nucleotides 311 to 751 of SEQ ID NO:1.

32. An isolated nucleic acid molecule which hybridizes under stringent hybridization conditions to a nucleic acid molecule comprising nucleotides 311 to 523 of SEQ ID NO:1.

33. An isolated nucleic acid molecule which hybridizes under stringent hybridization conditions to a nucleic acid molecule comprising nucleotides 533 to 751 of SEQ ID NO:1.

34. An isolated nucleic acid molecule comprising a nucleotide sequence which hybridizes under stringent hybridization conditions to the nucleotide sequence of SEQ ID NO:1.

35. An isolated nucleic acid molecule comprising a nucleotide sequence which hybridizes under stringent hybridization conditions to the nucleotide sequence of SEQ ID NO:3.

36. An isolated nucleic acid molecule comprising a nucleotide sequence which hybridizes under stringent hybridization conditions to the nucleotide sequence of the DNA insert of the plasmid deposited with ATCC as Accession Number 98546.

37. An isolated nucleic acid molecule at least 500 nucleotides in length which hybridizes under stringent hybridization conditions to a nucleic acid molecule comprising the nucleotide sequence of SEQ ID NO:1.

38. An isolated nucleic acid molecule at least 500 nucleotides in length which hybridizes under stringent hybridization conditions to a nucleic acid molecule comprising the nucleotide sequence of SEQ ID NO:3.

39. An isolated nucleic acid molecule at least 500 nucleotides in length which hybridizes under stringent hybridization conditions to a nucleic acid molecule comprising the nucleotide sequence of the DNA insert of the plasmid deposited with ATCC as Accession Number 98546.

40. The isolated nucleic acid molecule of claim 37, 38, or 39, which encodes an amino acid sequence which includes the follistatin cysteine-rich domain comprising amino acid residues 97 to 167 of SEQ ID NO:2 or the follistatin cysteine-rich domain comprising amino acid residues 171 to 243 of SEQ ID NO:2.

41. An isolated nucleic acid molecule comprising a nucleotide sequence encoding a polypeptide containing a follistatin cysteine-rich domain, wherein the nucleotide sequence is at least 55% identical to the nucleotide sequence of SEQ ID NO:1, SEQ ID NO:3, or the DNA insert of the plasmid deposited with ATCC as Accession Number 98546.

42. The isolated nucleic acid molecule of claim 41, wherein the nucleotide sequence is at least 75% identical to the nucleotide sequence of SEQ ID NO:1, SEQ ID NO:3, or the DNA insert of the plasmid deposited with ATCC as Accession Number 98546.

43. The isolated nucleic acid molecule of claim 42, wherein the nucleotide sequence is at least 85% identical to the nucleotide sequence of SEQ ID NO:1, SEQ ID NO:3, or the DNA insert of the plasmid deposited with ATCC as Accession Number 98546.

44. The isolated nucleic acid molecule of claim 43, wherein the nucleotide sequence is at least 95% identical to the nucleotide sequence of SEQ ID NO:1, SEQ ID NO:3, or the DNA insert of the plasmid deposited with ATCC as Accession Number 98546.

45. The isolated nucleic acid molecule of claim 41, 42, 43, or 44, wherein the polypeptide comprises an amino acid sequence which is at least 85% identical to the follistatin cysteine-rich domain selected from the group consisting of the follistatin-cysteine-rich domain comprising amino acid residues 97 to 167 of SEQ ID NO:2 and the follistatin cysteine-rich domain comprising amino acid residues 171 to 243 of SEQ ID NO:2.

46. The isolated nucleic acid molecule of claim 46, wherein the polypeptide comprises the follistatin cysteine-rich domain comprising amino acid residues 97 to 167 of SEQ ID NO:2 or the follistatin cysteine-rich domain comprising amino acid residues 171 to 243 of SEQ ID NO:2.

47. The isolated nucleic acid molecule of claim 41, 42, 43, or 44, wherein the polypeptide comprises an amino acid sequence which is at least 85% identical to the follistatin cysteine-rich domain comprising amino acid residues 97 to 167 of SEQ ID NO:2 and the follistatin cysteine-rich domain comprising amino acid residues 171 to 243 of SEQ ID NO:2.

48. The isolated nucleic acid molecule of claim 47, wherein the polypeptide comprises the follistatin cysteine-rich domain comprising amino acid residues 97 to 167 of SEQ ID NO:2 and the follistatin cysteine-rich domain comprising amino acid residues 171 to 243 of SEQ ID NO:2.

49. An isolated nucleic acid molecule comprising the nucleotide sequence of SEQ ID NO:1.

50. An isolated nucleic acid molecule comprising the nucleotide sequence of SEQ ID NO:3.

51. An isolated nucleic acid molecule comprising the nucleotide sequence of the DNA insert of the plasmid deposited with ATCC as Accession Number 98546.

52. An isolated nucleic acid molecule consisting of a nucleotide sequence which encodes a protein consisting of the amino acid sequence of SEQ ID NO:2.

53. An isolated nucleic acid molecule consisting of the nucleotide sequence of SEQ ID NO:1.

54. An isolated nucleic acid molecule consisting of the nucleotide sequence of SEQ ID NO:3.

55. An isolated nucleic acid molecule consisting of the nucleotide sequence of the DNA insert of the plasmid deposited with ATCC as Accession Number 98546.

56. A vector comprising the nucleic acid molecule of claim 1, 10, 13, 16–21, 23, 25, 29–39, 41–44, or 49–53.

57. The vector of claim 54, which is a recombinant expression vector.

58. A host cell containing the nucleic acid molecule of claim 1, 3, 10, 13, 16–21, 23 25, 27, 39, 41, or 49–53.

59. An isolated nucleic acid molecule which is antisense to the nucleic acid molecule of claim 1, 10, 13, 16–21, 23, 25, 27–39, 41–44, or 49–53.

60. A vector comprising the nucleic acid molecule of claim 59.

61. The vector of claim 60, which is an expression vector.

62. A host cell containing the nucleic acid molecule of claim 59.

63. A method for producing a polypeptide containing a follistatin cysteine-rich domain comprising culturing the host cell of claim 58 until the polypeptide is produced.

64. The method of claim 63, further comprising isolating the polypeptide from the medium or the host cell.

* * * * *